US009926346B2

(12) United States Patent
Fulkerson et al.

(10) Patent No.: US 9,926,346 B2
(45) Date of Patent: Mar. 27, 2018

(54) RECOMBINANT MYCOBACTERIUM ENCODING A HEPARIN-BINDING HEMAGGLUTININ (HBHA) FUSION PROTEIN AND USES THEREOF

(75) Inventors: John Fulkerson, Silver Spring, MD (US); Michael Brennan, Rockville, MD (US); Kamalakannan Velmurugan, Rockville, MD (US); Camille Locht, Brussels (BE)

(73) Assignees: Aeras, Rockville, MD (US); Institut National De La Sante Et De La Recherche Medicale (Inserm), Paris (FR)

( * ) Notice: Subject to any disclaimer, the term of this patent is extended or adjusted under 35 U.S.C. 154(b) by 249 days.

(21) Appl. No.: 14/394,689

(22) PCT Filed: Apr. 16, 2012

(86) PCT No.: PCT/US2012/033757
§ 371 (c)(1),
(2), (4) Date: Jun. 25, 2015

(87) PCT Pub. No.: WO2013/158061
PCT Pub. Date: Oct. 24, 2013

(65) Prior Publication Data
US 2015/0291669 A1    Oct. 15, 2015

(51) Int. Cl.
| C07K 14/35 | (2006.01) |
| A61K 39/04 | (2006.01) |
| A61K 49/00 | (2006.01) |
| A61K 39/00 | (2006.01) |

(52) U.S. Cl.
CPC .............. *C07K 14/35* (2013.01); *A61K 39/04* (2013.01); *A61K 49/0006* (2013.01); *A61K 2039/523* (2013.01); *A61K 2039/53* (2013.01); *C07K 2319/00* (2013.01); *C07K 2319/02* (2013.01); *C07K 2319/40* (2013.01); *C07K 2319/90* (2013.01)

(58) Field of Classification Search
None
See application file for complete search history.

(56) References Cited

U.S. PATENT DOCUMENTS

| 6,949,345 | B1 | 9/2005 | Menozzi et al. | |
| 7,625,572 | B2 | 12/2009 | Sun et al. | |
| 7,666,656 | B2 | 2/2010 | Sun et al. | |
| 7,745,141 | B2 | 6/2010 | Laal et al. | |
| 7,829,103 | B2 | 11/2010 | Pethe et al. | |
| 7,829,104 | B2 | 11/2010 | Sun et al. | |
| 8,012,467 | B2 | 9/2011 | Havenga et al. | |
| 8,043,857 | B2 | 10/2011 | Sun et al. | |
| 2002/0094336 | A1* | 7/2002 | Andersen ............... | C07K 14/35 424/190.1 |
| 2006/0292168 | A1 | 12/2006 | Pethe et al. | |
| 2008/0226678 | A1 | 9/2008 | McShane et al. | |
| 2009/0123438 | A1* | 5/2009 | Havenga ................. | A61K 39/04 424/93.21 |
| 2012/0034257 | A1 | 2/2012 | Pethe et al. | |

FOREIGN PATENT DOCUMENTS

| CN | 1966689 A | 5/2007 |
| EP | 2437061 | 4/2012 |
| WO | 9844119 | 10/1998 |
| WO | 2011013097 | 2/2011 |
| WO | 2011144951 | 11/2011 |

OTHER PUBLICATIONS

He et al. 2011 (Assessment of Five Antigens from *Mycobacterium tuberculosis* for Serodiagnosis of Tuberculosis; Clinical and Vaccine Immunology 18(4):565-570).*
Chapman et al. 2010 (Recombinant Mycobacterium bovis BCG as an HIV Vaccine Vector; Curr HIV Res 8(4): 282-298).*
Sun et al. 2009 (Novel recombinant BCG expressing perfringolysin O and the over-expression of key immunodominant antigens; preclinical characterization, safety and protection against challenge with *Mycobacterium tuberculosis*; Vaccine 27: 4412-4423).*
He et al., Assessment of give antigens from *Mycobacterium tuberculosis* for serodiagnosis of tuberculosis, Clinical and Vaccine Immunology 2011 18(4):565-570.
Pethe et al., "The heparin-binding haemagglutinin of M. tuberculosis is required for extrapulmonary dissemination", Nature, Jul. 12, 2001;412(6843):190-4.
Temmerman et al., "Methylation-dependent T cell immunity to *Mycobacterium tuberculosis* heparin-binding hemagglutinin", Nat Med, Sep. 2004;10(9):935-41.
Zanetti et al., "Patients with pulmonary tuberculosis develop a strong humoral response against methylated heparin-hinding hemagglutinin", Clin Diagn Lab Immunol, Sep. 2005; 12(9):1135-8.
Sun et al., Novel recombinant BCG expressing perfringolysin O and the over-expression of key immunodominant antigens; pre-clinical characterization, safety and protection against challenge with *Mycobacterium tuberculosis*, Vaccine, Jul. 16, 2009; 27(33):4412-23.
Rouse et al., "Immunological characterization of recombinant antigens isolated from a *Mycobacterium avium* lambda gt11 expression library by using monoclonal antibody probes", Infect Immun, Aug. 1991; 59(8):2595-600.
Pethe et al., "Mycobacterial heparin-hinding hemagglutinin and laminin-binding protein share antigenic methyllsyines that confer resistance to proteolysis", PNAS, 2002, 99(16):10759-64.
Hougardy et al., Heparin-binding-hemagglutinin-induced IFN-gamma release as a diagnostic tool for latent tuberculosis, PLoS One, Oct. 3, 2007; 2(10):e926.
Liu et al., Construction, expression and identification of recombinant bacillus Calmette-Guerin vaccine secreting huma nterferon alpha-2a, Natl Med J China 2006 86(34)2417-2420.

* cited by examiner

*Primary Examiner* — Mary Lyons
(74) *Attorney, Agent, or Firm* — Stradley Ronon Stevens & Young, LLP

(57) ABSTRACT

Recombinant *Mycobacteria* (rMyc) which contain sequences encoding a heparin-binding hemagglutinin (HBHA) fusion protein are provided, as are methods of making and using the rMyc and the fusion protein. The fusion protein includes an amino terminal mycobacterial antigen Ag85B leader peptide and transcription of the fusion protein is driven by an Ag85B promoter sequence. The recombinant fusion protein is produced in abundance by the rMyc, is post-translationally methylated, and is highly antigenic.

17 Claims, 13 Drawing Sheets

A.

| | |
|---|---|
| atgagacgac tttgcgcccg aatcgacatt tggcctccac acacggtatg ttctggcccg | 60 |
| agcacacgac gacatacagg acaaagggc acaagtatgg ccacagacgt gagccgaaag | 120 |
| attcgagctt ggggacgccg attgatgatc ggcacggcag cggctgtagt ccttccgggc | 180 |
| ctggtggggc ttgccggcgg agcggcaacc gcgggcgcgt tctccatggc tgaaaactcg | 240 |
| aacattgatg acatcaaggc tccgttgctt gccgcgcttg gagcggccga cctggccttg | 300 |
| gccactgtca acgagttgat cacgaacctg cgtgagcgtg cggaggagac tgtacggac | 360 |
| acccgcagcc gggtcgagga gagccgtgct cgcctgacca agctgcagga agatctgccc | 420 |
| gagcagctca ccgagctgcg tgagaagttc accgccgagg agctgcgtaa ggccgcgag | 480 |
| ggctacctcg aggccgcgac tagccggtac aacgagctgg tcgagcgcgg tgaggccgct | 540 |
| ctagagcggc tgcgcagcca gcagagcttc gaggaagtgt cggcgcgcgc cgaaggctac | 600 |
| gtggaccagg cggtggagtt gacccaggag gcgttgggta cggtcgcatc gcagacccgc | 660 |
| gcggtcggtg agcgtgccgc caagctggtc ggcatcgagc tgcctaagaa ggctgctccg | 720 |
| gccaagaagg ccgctccggc caagaaggcc gctccggcca agaaggcggc ggccaagaag | 780 |
| gcgcccgcga agaaggcggc ggccaagaag gtcacccaga agtag | 825 |

(SEQ ID NO: 1)

B.

| | |
|---|---|
| gtggtcttcg tcggcttgct tcgagcgagc ctacgcggtg aacgcaagtt cggcctccct | 60 |
| gggggagcac agccggtagc cccgggccgc gattctgaga aatccgcgat agatccatac | 120 |
| cgccataccg tttgtgagcc ccctaagcac acttgctctg tccgcggcgg taaccgatac | 180 |
| ggaaatgaga cgactttgcg cccgaatcga catttggcct ccacacacgg tatgttctgg | 240 |
| cccgagcaca cgacgacata caggacaaag gggcacaagt atggccacag acgtgagccg | 300 |
| aaagattcga gcttggggac gccgattgat gatcggcacg gcagcggctg tagtccttcc | 360 |
| gggcctggtg ggcttgccg gcggagcggc aaccgcgggc gcgttctcc atggctgaaaa | 420 |
| ctcgaacatt gatgacatca aggctccgtt gcttgccgcg cttggagcgg ccgacctggc | 480 |
| cttggccact gtcaacgagt tgatcacgaa cctgcgtgag cgtgcggagg agactcgtac | 540 |
| ggacacccgc agccgggtcg aggagagccg tgctcgcctg accaagctgc aggaagatct | 600 |
| gcccgagcag ctcaccgagc tgcgtgagaa gttcaccgcc gaggagctgc gtaaggccgc | 660 |
| cgagggctac ctcgaggccg cgactagccg gtacaacgag ctggtcgagc gcggtgaggc | 720 |
| cgctctagag cggctgcgca gccagcagag cttcgaggaa gtgtcggcgc gcgccgaagg | 780 |
| ctacgtggac caggcggtgg agttgaccca ggaggcgttg ggtacggtcg catcgcagac | 840 |
| ccgcgcggtc ggtgagcgtg ccgccaagct ggtcggcatc gagctgccta agaaggctgc | 900 |
| tccggccaag aaggccgctc cggccaagaa ggccgctccg gccaagaagg cggcggccaa | 960 |
| gaaggcgccc gcgaagaagg cggcggccaa gaaggtcacc cagaagtag | 1009 |

(SEQ ID NO: 2)

Figure 1A and B

A.
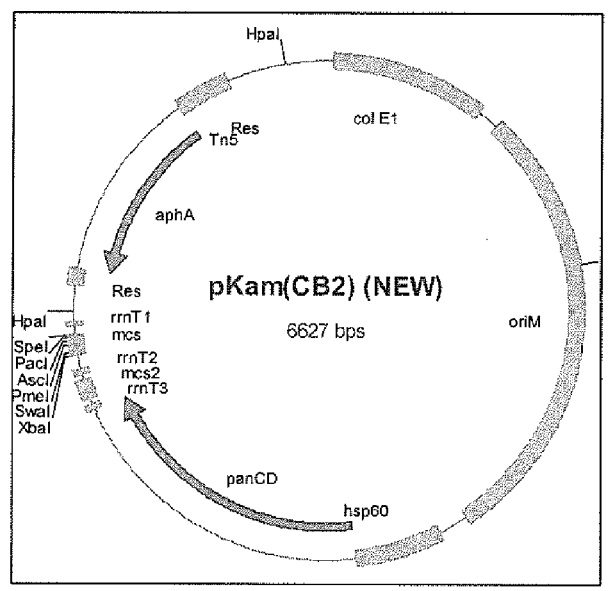
B.
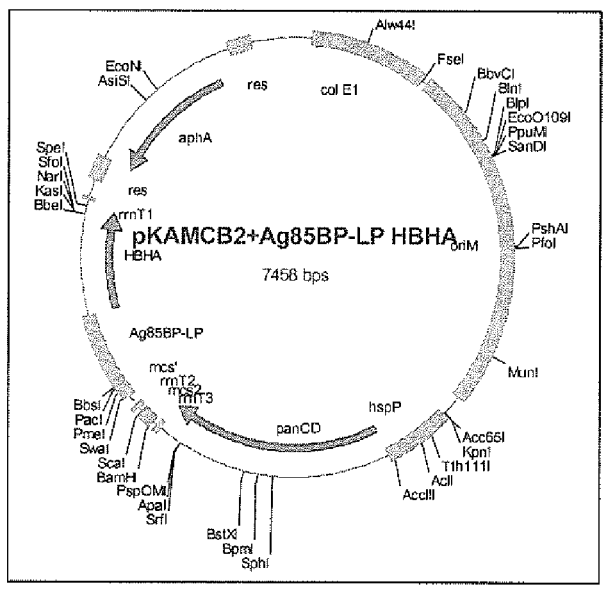
Figure 3A and B

A.

AERAS-445 HBHA aa
  1 mrrlcaridi wpphtvcsgp strrhtgqrg tsmatdvsrk irawgrrlmi
 51 gtaaavvlpg lvglaggaat agafsmaens niddikapll aalgaadlal
101 atvnelitnl reraeetrtd trsrveesra rltklqedlp eqltelrekf
151 taeelrkaae gyleaatsry nelvergeaa lerlrsqqsf eevsaraegy
201 vdqaveltqe algtvasqtr avgeraaklv gielpkkaap akkaapakka
251 apakkaaakk apakkaaakk vtqk (SEQ ID NO: 3)

B.

BCG HBHA aa
  1 aensniddik apllaalgaa dlalatvnel itnlreraee trtdtrsrve
 51 esrarltklq edlpeqltel rekftaeelr kaaegyleaa tsrynelver
101 geaalerlrs qqsfeevsar aegyvdqave ltqealgtva sqtravgera
151 aklvgielpk kaapakkaap akkaapakka aakkapakka aakkvtqk (SEQ ID NO: 4)

C.

```
445-HBHAaa (1 to 274)                          Homology Block: 76 to 274

N:——85B Leader——━━━━━━━━━━━━━━━━━━━━━━━━━━━━:C
                  N:━━━━━━━━━━━━━━━━━━━━━━━━━━━━━:C BCG-HBHAaa (1 to 199)                          Homology Block: 1 to 199
```

Figure 5A-C

A
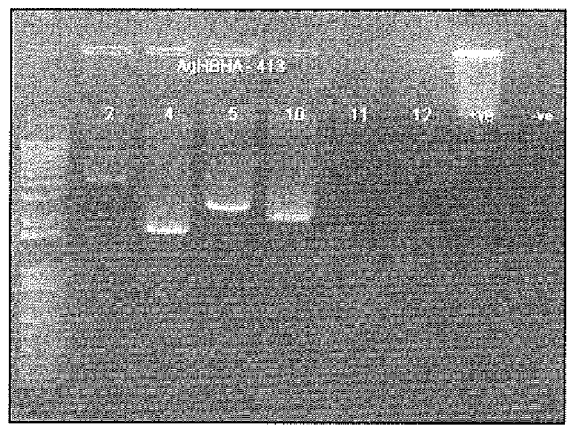
B
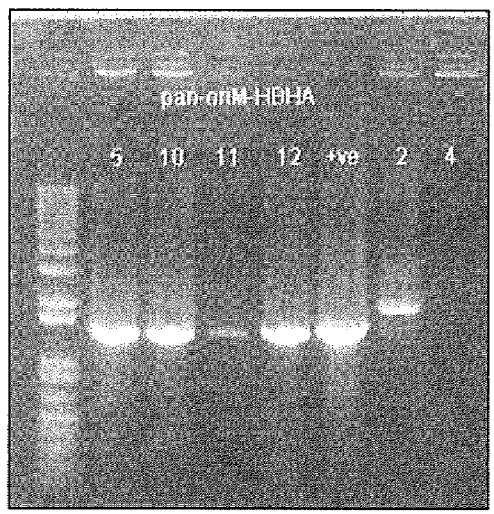
Figure 6A and B

C

A.
B.
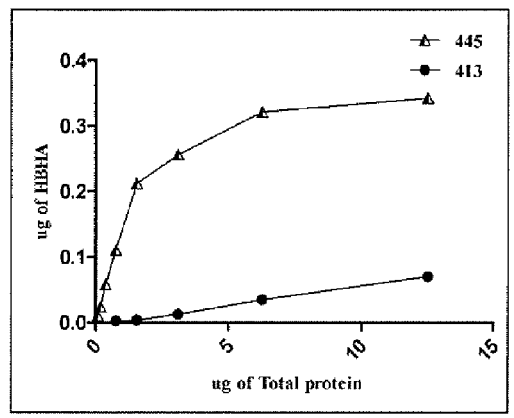
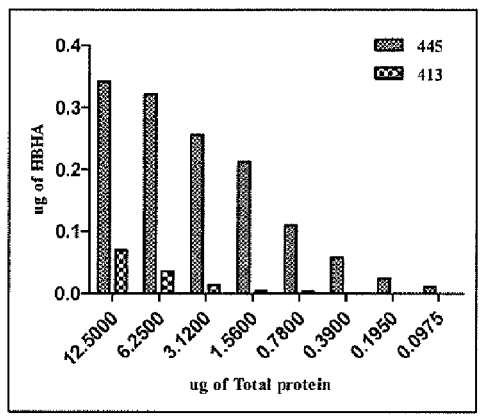
Figure 11
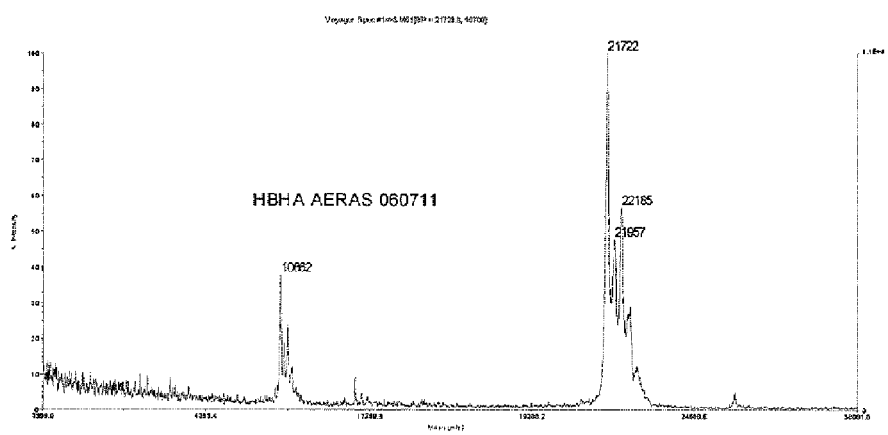
Figure 12

A.
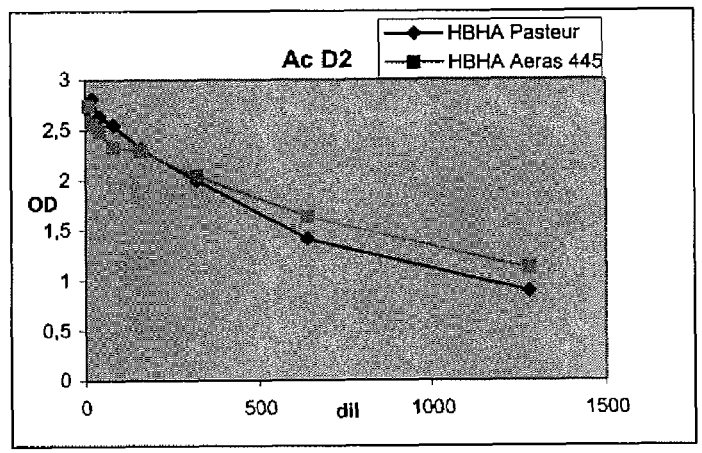
B.
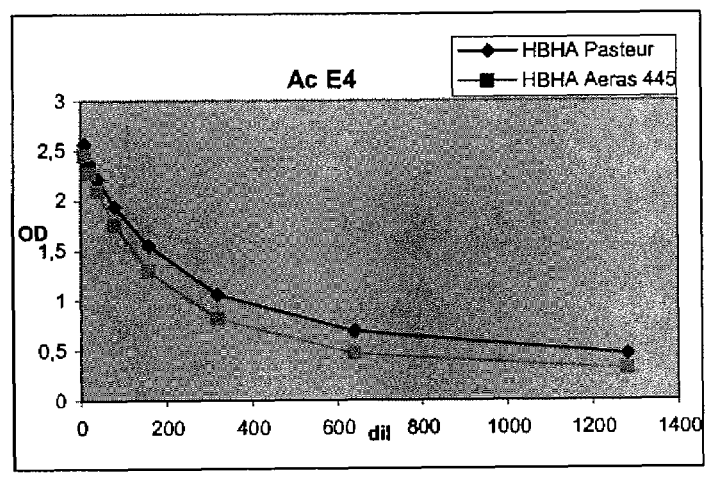
Figure 14A and B

RECOMBINANT MYCOBACTERIUM ENCODING A HEPARIN-BINDING HEMAGGLUTININ (HBHA) FUSION PROTEIN AND USES THEREOF

BACKGROUND OF THE INVENTION

Field of the Invention

The invention generally relates to recombinant *Mycobacteria* which contain and express sequences encoding a heparin-binding hemagglutinin (HBHA) fusion protein. The fusion protein contains an amino terminal mycobacterial antigen Ag85B leader sequence, and transcription of the fusion protein is driven by a suitable promoter, e.g. the Ag85B promoter. The invention also provides methods of making and using the recombinant *Mycobacteria* and the recombinant fusion protein, e.g. as vaccinogens.

Background of the Invention

Tuberculosis (TB) is a global public health problem resulting in 8 million new cases and 2 million deaths each year. A particularly problematic aspect of TB diagnosis and treatment is the ability of the *Mycobacterium tuberculosis* (Mtb) *bacillus* to enter a latent, asymptomatic state and to persist in latently infected individuals for long periods of time. Such individuals are susceptible to reactivation of the disease due to, for example, immune suppression caused by diseases or conditions such as HIV, treatments such as chemotherapy and the use of corticosteroids, the waning of immunity that accompanies aging, etc. An estimated 2 billion persons (one-third of the world's population) are latently infected with Mtb at present, and activation of latent tuberculosis accounts for most new cases of active disease. Reactivation is associated with inflammation, necrosis and cavitation of the lung, a process that results in draining of the lesions into the bronchus. Aerosols generated when individuals with bronchial lesions cough causes dissemination of the Mtb organism to uninfected, susceptible persons, and the transmission cycle is thus maintained.

The only currently available vaccine against TB, *Mycobacterium bovis* (Bacille Calmette-Guérin) (BCG), was first introduced in 1921. BCG has been widely utilized and while studies show that for some purposes BCG is effective (e.g. against disseminated TB), it is known to be ineffective with respect to preventing the development, persistence and reactivation of latent TB.

There is an ongoing need to develop improved, more effective vaccines against TB. In particular, there is a need to develop vaccines that provide protection against the development, maintenance and/or reactivation of latent tuberculosis infection.

One protein that has been proposed for use in TB vaccines is the heparin-binding hemagglutinin (HBHA) protein. HBHA is a 22-kDa, methylated, surface-exposed protein that mediates the interaction of the tubercle *bacilli* with the host, acting as an adhesin for nonphagocytic cells. Methylation of the C-terminal lysine residues is known to affect both the biochemical and immunological properties of the protein, and several experimental findings have implicated HBHA in the process of extrapulmonary dissemination of Mtb (Pethe et al., 2001. Nature 412:190-194.). Temmerman et al. (Nature Medicine 10, 935-941 (2004)) showed that covalent methylation of HBHA is necessary for the elicitation of a protective T cell response in mice challenged with Mtb, and Zannetti et al. showed that purified methylated HBHA is strongly recognized by sera obtained from TB patients compared to controls, whereas unmethylated HBHA is not (Clin Diagn Lab Immunol September 2005 vol. 12 no. 9 1135-1138). In light of these and other studies, it has been proposed that the development of an HBHA-based vaccine may represent an effective strategy to prevent and/or treat TB.

U.S. Pat. No. 7,829,103 to Pethe et al., the complete contents of which is hereby incorporated by reference in entirety, reports immunogenic compositions comprising methylated recombinant HBHA. According to Pethe, the HBHA may be produced by one of two methods: either by 1) producing recombinant non-methylated HBHA protein in a heterologous cell (*Escherichia coli* or *Mycobacterium smegmatis*) and then post-translationally methylating the purified recombinant HBHA using a chemical or enzymatic method; or 2) using a recombinant cell to co-express nucleotide sequences encoding HBHA and a mycobacterial methyltransferase. Method 1 involves multiple steps for protein preparation; method 2 involves the use of a heterologous cell that is not administrable as a vaccine. Further, the bacterial strains employed by Pethe were antibiotic resistant, and no discussion of optimizing protein yields is provided. Thus, there remains a need in the art for a recombinant Mtb that is capable of being used as a vaccinogen, and/or for producing sufficient quantities of HBHA to be clinically relevant, both in vitro and in vivo, and/or for producing large quantities of HBHA in a manufacturing setting for later use in clinical applications.

SUMMARY OF THE INVENTION

The invention provides recombinant *Mycobacteria* (rMyc) which contain and express nucleic acid sequences encoding a heparin-binding hemagglutinin (HBHA) fusion protein. The fusion protein includes a mycobacterial antigen Ag85B leader peptide attached at the amino terminus. The fusion protein is post-translationally methylated, resulting in a protein with a methylation pattern that is the same as or highly similar to that of native HBHA. The resulting fusion protein is thus highly antigenic, and copious amounts of the highly antigenic fusion protein can be produced using the methods of the invention. Transcription of the fusion protein is driven by a suitable promoter, which can be constitutive or inducible. In one embodiment, the promoter is the Ag85B promoter sequence, The invention also provides methods of making the rMyc (e.g on an industrial scale), methods of using the rMyc e.g. as a vaccinogen and/or to elicit an immune response, or to make the fusion protein; or to produce seed cultures; and methods of making and using the fusion protein e.g. as a vaccinogen and/or to elicit an immune response, or as a diagnostic, for example, to detect latent tuberculosis infections.

It is an object of this invention to provide a recombinant *Mycobacterium* that is genetically engineered to contain and express a nucleic acid fusion sequence encoding an Ag85B leader sequence attached to an amino teminus of a mycobacterial heparin-binding haemagglutinin (HBHA) protein, the fusion sequence being operably linked to a promoter. In some embodiments, the *Mycobacterium* is, for example, *Mycobacterium tuberculosis, Mycotabcterium bovis*, or *Mycobacterium smegmatis*. In other embodiments, the *Mycobacterium* is *Mycobacterium bovis* e.g. *Mycobacterium bovis* (Bacille Calmette-Guérin) (BCG). In some embodiments, the BCG is a BCG Danish Statens Serum Institut (SSI) strain and may, for example, express a pfo gene such as a pfo gene from *Clostridium perfringens*. In some embodiments, the *Mycobacterium* is an auxotroph, for example, a pantothenic acid auxotroph.

In some embodiments of the invention, the nucleic acid fusion sequence is

```
                                       (SEQ ID NO: 1)
atgagacgac tttgcgcccg aatcgacatt tggcctccac acacggtatg ttctggcccg agcacacgac gacatacagg acaaagggc acaagtatgg ccacagacgt gagccgaaag attcgagctt ggggacgccg attgatgatc ggcacggcag cggctgtagt ccttccgggc ctggtggggc ttgccggcgg agcggcaacc gcgggcgcgt tctccatggc tgaaaactcg aacattgatg acatcaaggc tccgttgctt gccgcgcttg gagcggccga cctggccttg gccactgtca acgagttgat cacgaacctg cgtgagcgtg cggaggagac tcgtacggac acccgcagcc gggtcgagga gagccgtgct cgcctgacca agctgcagga agatctgccc gagcagctca ccgagctgcg tgagaagttc accgccgagg agctgcgtaa ggccgccgag ggctacctcg aggccgcgac tagccggtac aacgagctgg tcgagcgcgg tgaggccgct ctagagcggc tgcgcagcca gcagagcttc gaggaagtgt cggcgcgcgc cgaaggctac gtggaccagg cggtggagtt gacccaggag gcgttgggta cggtcgcatc gcagacccgc gcggtcggtg agcgtgccgc caagctggtc ggcatcgagc tgcctaagaa ggctgctccg gccaagaagg ccgctccggc caagaaggcc gctccggcca agaaggcggc ggccaagaag gcgcccgcga agaaggcggc ggccaagaag gtcacccaga agtag.
```

In other embodiments, the polypeptide encoded by the nucleic acid fusion sequence has an amino acid sequence: mrrlcaridi wpphtvcsgp strrhtgqrg tsmatdvsrk irawgrrlmi gtaaavvlpg lvglaggaat agafsmaens niddikapll aalgaadlal atvnelitnl reraeetrtd trsrveesra rltklqedlp eqltelrekf taeelrkaae gyleaatsry nelvergeaa lerlrsqqsf eevsaraegy vdqaveltqe algtvasqtr avgeraaklv gielpkkaap akkaapakka apakkaaakk vtqk (SEQ ID NO: 3).

In some embodiments, the mycobacterial HBHA protein is *Mycobacterium tuberculosis* HBHA. In yet other embodiments, the promoter is a mycobacterial Ag85B promoter The invention also provides an isolated recombinant nucleic acid molecule with a nucleotide sequence:

```
                                       (SEQ ID NO: 1)
atgagacgac tttgcgcccg aatcgacatt tggcctccac acacggtatg ttctggcccg agcacacgac gacatacagg acaaagggc acaagtatgg ccacagacgt gagccgaaag attcgagctt ggggacgccg attgatgatc ggcacggcag cggctgtagt ccttccgggc ctggtggggc ttgccggcgg agcggcaacc gcgggcgcgt tctccatggc tgaaaactcg aacattgatg acatcaaggc tccgttgctt gccgcgcttg gagcggccga cctggccttg gccactgtca acgagttgat
```

-continued

```
cacgaacctg cgtgagcgtg cggaggagac tcgtacggac acccgcagcc gggtcgagga gagccgtgct cgcctgacca agctgcagga agatctgccc gagcagctca ccgagctgcg tgagaagttc accgccgagg agctgcgtaa ggccgccgag ggetacctcg aggccgcgac tagccggtac aacgagctgg tcgagcgcgg tgaggccgct ctagagcggc tgcgcagcca gcagagcttc gaggaagtgt cggcgcgcgc cgaaggctac gtggaccagg cggtggagtt gacccaggag gcgttgggta cggtcgcatc gcagacccgc gcggtcggtg agcgtgccgc caagctggtc ggcatcgagc tgcctaagaa ggctgctccg gccaagaagg ccgctccggc caagaaggcc gctccggcca agaaggcggc ggccaagaag gcgcccgcga agaaggcggc ggccaagaag gtcacccaga agtag.
```

The invention also provides a recombinant fusion protein which comprises an Ag85B leader sequence covalently attached to an amino terminus of a mycobacterial heparin-binding haemagglutinin (HBHA) protein. In one embodiment, the entire fusion protein is transcribed as one mRNA and translated as a single polypeptide (protein). In one embodiment, the recombinant fusion protein has an amino acid sequence: mrrlcaridi wpphtvcsgp strrhtgqrg tsmatdvsrk irawgrrlmi gtaaavvlpg lvglaggaat agafsmaens niddikapll aalgaadlal atvnelitnl reraeetrtd trsrveesra rltklqedlp eqltelrekf taeelrkaae gyleaatsry nelvergeaa lerlrsqqsf eevsaraegy vdqaveltqe algtvasqtr avgeraaklv gielpkkaap akkaapakka apakkaaakk. vtqk (SEQ ID NO: 3). In some embodiments, the recombinant fusion protein is methylated.

The invention also provides methods of producing a recombinant fusion protein that comprises an Ag85B leader sequence attached to an amino teminus of a mycobacterial heparin-binding haemagglutinin (HBHA) protein. The method comprises: 1) transfecting a bacterial cell such as a *Mycobacterium* cell with a nucleic acid sequence encoding the recombinant fusion protein; 2) growing the transfected bacterium (e.g. a *Mycobacterium*) cell under conditions which allow the bacterium cell to produce the recombinant fusion protein; and 3) obtaining the recombinant fusion protein. In some embodiments, the transfecting is carried out by electroporation.

The invention also provides methods of determining whether a subject has a latent tuberculosis infection. The method comprises determining the presence or absence of immune reactivity of the patient to a recombinant fusion protein comprising an Ag85B leader sequence attached to an amino terminus of a mycobacterial heparin-binding haemagglutinin (HBHA) protein. The presence of immune reactivity indicates that the subject has a latent tuberculosis infection. Determining the presence or absence of immune reactivity may include, for example, 1) obtaining a biological sample from the subject, and 2) detecting the presence or absence of immune reactivity in the biological sample. Exemplary biological samples include but are not limited to sputum samples and serum samples. In other embodiments, determining the presence or absence of immune reactivity may include the step of detecting includes 1) intradermally injecting the recombinant fusion protein into the subject, and 2) determining the presence or absence of immune reactivity at the site of intradermal injection.

The invention also provides methods of eliciting an immune response against *Mycobacterium tuberculosis* in a subject in need thereof. This method comprises the step of administering to the subject an amount of a recombinant fusion protein comprising an Ag85B leader sequence attached to an amino terminus of a mycobacterial heparin-binding haemagglutinin (HBHA) protein sufficient to elicit an immune response in said subject, and may be referred to as a "therapeutic" amount. In one embodiment, the immune response that is elicited is production of one or more of B cells, antibodies and T cells. In some embodiments, the immune response is a protective immune response.

The invention also provides methods of eliciting an immune response against *Mycobacterium tuberculosis* in a subject in need thereof. The method comprises administering to the subject a recombinant *Mycobacterium* comprising a nucleic acid fusion sequence encoding an Ag85B leader sequence attached to an amino terminus of a mycobacterial heparin-binding haemagglutinin (HBHA) protein. The fusion sequence is operably linked to a promoter, and the recombinant *Mycobacterium* is administered in an amount sufficient to elicit an immune response in the subject. In one embodiment, the immune response is production of antibodies. In some embodiments, the immune response is a protective immune response.

The invention also provides methods of producing recombinant heparin-binding haemagglutinin (rHBHA) protein. The methods comprise 1) growing a culture of recombinant *Mycobacteria* comprising a nucleic acid fusion sequence encoding an Ag85B leader sequence attached to an amino terminus of a mycobacterial heparin-binding haemagglutinin (HBHA) protein, wherein said fusion sequence is operably linked to a promoter, under conditions in which the rHBHA is produced. In some embodiments, the method further comprises obtaining the rHBHA protein from the culture. The method may also include purifying the rHBHA protein, e.g. after the step of obtaining the rHBHA. Purifying may be carried out using one or more physico-chemical technologies such as, for example, chromatography (e.g. one or more of affinity, size exclusion, ion exchange, or hydrophobic interaction chromatography); and/or cell disruption techniques (e.g. one or more of high pressure cell disruption, bead beaters, homogenization, sonication, centrifugation, and the like). The method may also include verifying the identity of the rHBHA protein. In some embodiments, the step of growing is carried out in culture by shaking or by fermentation. In some embodiments, growing is carried out using a batch or a continuous culture.

The invention further provides seed lots of recombinant *Mycobacterium*. In some embodiments, a seed lot comprises 1) recombinant *Mycobacteria* comprising a nucleic acid fusion sequence encoding an Ag85B leader sequence attached to an amino terminus of a mycobacterial heparin-binding haemagglutinin (HBHA) protein, wherein the fusion sequence is operably linked to a promoter; and 2) medium suitable for maintaining the recombinant *Mycobacteria* in a viable state during storage of the seed lot.

The invention also provides methods of preparing a composition comprising a heparin-binding haemagglutinin (HBHA) protein. In some embodiments, the method comprises 1) growing a culture of recombinant *Mycobacteria* comprising a nucleic acid fusion sequence encoding an Ag85B leader sequence attached to an amino terminus of a mycobacterial heparin-binding haemagglutinin (HBHA) protein, wherein the fusion sequence is operably linked to a promoter; 2) obtaining the rHBHA protein from the culture; 3) purifying the rHBHA protein; and 4) combining purified rHBHA protein with a physiologically acceptable carrier. The growing may be carried out in shake culture or by fermentation. In addition, method may further comprise adding one or more additional therapeutically useful agents, including but not limited to, one or more antigens that are not HBHA, one or more adjuvants, and one or more immunogenicity enhancers, to the rHBHA and physiologically acceptable carrier. These compositions may be used, for example, as a vaccine, a therapeutic or a diagnostic, or for any other purpose.

BRIEF DESCRIPTION OF THE DRAWINGS

FIGS. 1A and B. A, DNA sequence (SEQ ID NO:1) encoding the HBHA fusion protein. The Ag85B leader peptide is encoded by the underlined nucleotides. B, DNA sequence encoding the HBHA fusion protein as in A but also showing the exemplary Ag85B promoter sequence in bold (SEQ ID NO:2).

FIGS. 3A and B. Schematic showing A, the pantothenate complementation plasmid (pKAMCB2) and B, cloning of HBHA gene into pKAMCB2.

FIG. 5A-C. Amino acid sequencing of A, recombinant HBHA (SEQ ID NO: 3) compared with B, native HBHA from which amino terminal methionine has been cleaved (SEQ ID NO: 4) and C, schematic showing position of Ag85B leader at N-terminus.

FIG. 6A-C. Recombinant BCG colonies PCR screened for A, the HBHA gene, B, presence of plasmid backbone and C, absence of kanamycin resistance marker. Clone no. 5 tested positive for the presence of HBHA gene, intact plasmid backbone and the absence of kanamycin gene.

FIG. 12. Mass spectrometry analysis of rHBHA purified from AERAS 445

FIG. 14 Antigenicity analysis by ELISA using monoclonal antibodies 3921E4; A and 4057D2; B

DETAILED DESCRIPTION

Figure 2:
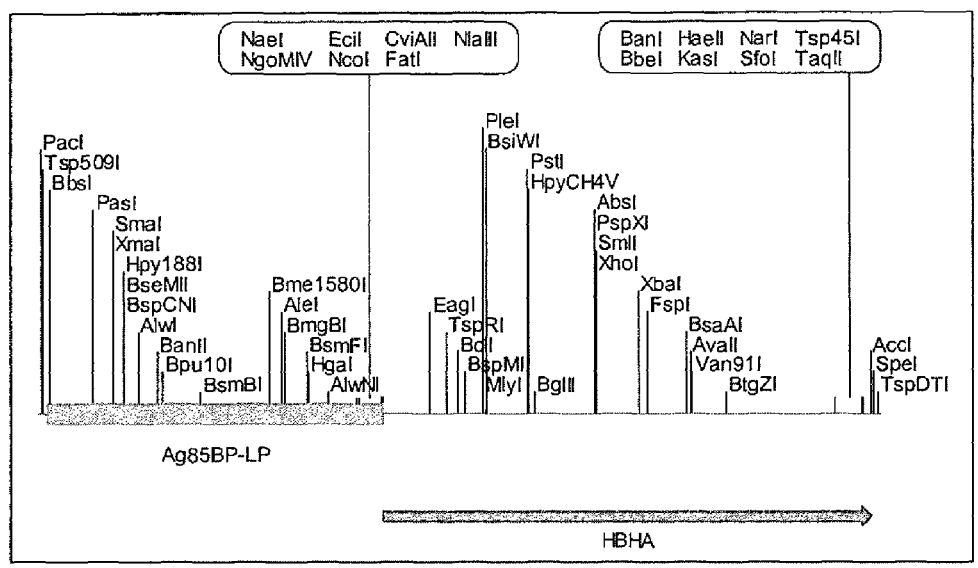
FIG. 2. In silico cloning and complementation strategy.

In one embodiment, the invention provides recombinant *Mycobacteria* (rMyc) which contain and express nucleic acid sequences encoding a heparin-binding hemagglutinin (HBHA) fusion protein. The recombinant *Mycobacteria* can be administered in vaccine preparations since they are not antibiotic resistant and are attenuated. The fusion protein includes, attached to its amino terminus, a mycobacterial antigen Ag85B leader peptide sequence. The rMycs of the invention produce large amounts of the fusion protein, with transcription being driven by a suitable promoter. The fusion protein may also be recovered from the rMyc in an industrial manufacturing process and be used as part of a vaccine preparation or diagnostic.

In one embodiment, the nucleic acid sequence that encodes the antigenic recombinant fusion protein of the invention is the DNA sequence depicted in FIG. 1A (SEQ ID NO: 1) As can be seen, the nucleic acid encodes the Ag85B leader sequence at nucleotides 1 to 225 (underlined) and the HBHA protein at nucleotides 226 to 825. In addition, in the exemplary embodiment depicted in FIG. 1B, at its 5' end, the nucleic acid contains the Ag85B promoter sequence at nucleotides 1 to 184 (shown in bold). In the embodiment illustrated in FIG. 1B, the translated fusion protein per se that is produced by the cell is thus encoded by nucleotides 185 to 1009, i.e. the promoter region is not translated.

In one embodiment, the invention encompasses a nucleic acid with a sequence which is or which includes the sequence as set forth in SEQ ID NO: 1 (see FIG. 1A). In another embodiment, the invention encompasses a nucleic acid with a sequence that is or includes the sequence as set forth in SEQ ID NO: 2 (see FIG. 1B). In another embodiment, the invention encompasses a nucleic acid with a sequence that is or includes the sequence as set forth in SEQ ID NO: 3 (see below). The invention also encompasses DNA that is complementary to SEQ ID NOS: 1 and 2, and also mRNA that is translated from SEQ ID NOS: 1 and 2 (or complements thereof), or cDNA based on such mRNA (as well as various DNA-RNA hybrids of these), and encompasses both single and double stranded nucleic acids. Further, those of skill in the art will recognize that, in order to produce an antigenic recombinant fusion protein as described herein (i.e. comprising an Ag85B leader sequence attached to an amino terminus of a mycobacterial HBHA protein), the precise sequence of SEQ ID NOS: 1 and 2 need not be employed. For example, sequences with at least about 75, 80, 85, 90, 91, 92, 93, 94, 95, 96, 97, 98, or about 99% homology to SEQ ID NOS: 1 and 2 may also be employed, so long as the translated polypeptide is able to be methylated and is sufficiently antigenic to elicit an immune response in a subject to whom it is administered. These levels of homology are also applicable to the corresponding complementary DNA, RNA, etc. described above. Those of skill in the art are familiar with automated programs or software for determining homology levels. In addition, those of skill in the art will recognize that the nucleic acid sequence that encodes the fusion protein may also include various helpful sequences, e.g. restriction sites for ease of genetic manipulation of the sequence. The % homologies described herein can be determined, for example, using the Smith-Waterman homology search algorithm as implemented in MSPRCH program (Oxford Molecular) using anaffine gap search with the following search parameters: gap open penalty of 12, and gap extension penalty of 1.

Exemplary variations of the recombinant sequence include but are not limited to: the substitution of codons which encode conservative amino acid replacements of some encoded residues; the insertion of e.g. sequences encoding linker or spacer sequences, e.g. between the promoter and the leader sequence, or between the leader sequence and the HBHA encoding sequence; various changes to the sequence to facilitate handling or manipulation of the sequence, e.g. the insertion of or change in restriction enzyme sites which flank the sequence; portions of a vector (e.g. 5' or 3' overhangs or sequences complementary to the same), sequences which encode various tags as described below, etc. This is illustrated in the sequence of SEQ ID NO: 3, where additional non-coding sequences at the 5' and 3' ends of the sequence are shown in italics, and the bold and underlined sequences represent promoter region and a leader peptide, as described above.

(SEQ ID NO: 12)
*ACTGTTAATTAAG*TGGTCTTCGTCGGCTTGCTTCGAGCGAGCCTACGCGG
TGAACGCAAGTTCGGCCTCCCTGGGGGAGCACAGCCGGTAGCCCCGGGC
CGCGATTCTGAGAAATCCGCGATAGATCCATACCGCCATACCGTTTGTGA
GCCCCCTAAGCACACTTGCTCTGTCCGCGGCGGTAACCGATACGGAAATG
AGACGACTTTGCGCCCGAATCGACATTTGGCCTCCACACACGGTATGTTC
TGGCCCGAGCACACGACGACATACAGGACAAAGGGGCACAAGTATGGCCA
CAGACGTGAGCCGAAAGATTCGAGCTTGGGGACGCCGATTGATGATCGGC
ACGGCAGCGGCTGTAGTCCTTCCGGGCCTGGTGGGGCTTGCCGGCGGAGC
GGCAACCGCGGGCGCGTTCTCCATGGCTGAAAACTCGAACATTGATGACA
TCAAGGCTCCGTTGCTTGCCGCGCTTGGAGCGGCCGACCTGGCCTTGGCC
ACTGTCAACGAGTTGATCACGAACCTGCGTGAGCGTGCGGAGGAGACTCG
TACGGACACCCGCAGCCGGGTCGAGGAGAGCCGTGCTCGCCTGACCAAGC
TGCAGGAAGATCTGCCCGAGCAGCTCACCGAGCTGCGTGAGAAGTTCACC
GCCGAGGAGCTGCGTAAGGCCGCCGAGGGCTACCTCGAGGCCGCGACTAG
CCGGTACAACGAGCTGGTCGAGCGCGGTGAGGCCGCTCTAGAGCGGCTGC
GCAGCCAGCAGAGCTTCGAGGAAGTGTCGGCGCGCGCCGAAGGCTACGTG
GACCAGGCGGTGGAGTTGACCCAGGAGGCGTTGGGTACGGTCGCATCGCA
GACCCGCGCGGTCGGTGAGCGTGCCGCCAAGCTGGTCGGCATCGAGCTGC
CTAAGAAGGCTGCTCCGGCCAAGAAGGCCGCTCCGGCCAAGAAGGCCGCT
CCGGCCAAGAAGGCGGCGGCCAAGAAGGCGCCCGCGAAGAAGGCGGCGGC
CAAGAAGGTCACCCAGAAGTAG*ACTAGTTCAT*.

Expression of the fusion protein is driven by a promoter sequence that is operably linked to SEQ ID NO: 1. By "operably linked" it is meant that the promoter sequence and SEQ ID NO: 1 are arranged within a nucleic acid molecule such that expression of SEQ ID NO: 1 is driven or controlled by the promoter. In some embodiments, the promoter may directly precede SEQ ID NO: 1 in the molecule. In other embodiments, some additional sequences may intervene. In addition, other control elements that aid in expression of SEQ ID NO: 1 may also be included in the nucleic acid molecule, e.g. various enhancer sequences, etc. Exemplary promoters that may be used in the practice of the invention include but are not limited to, for example, promoters of genes hsp60, hspX, pBlaF or mtrA, etc. In one embodiment, the promoter is the Ag85B promoter, and is arranged with respect to SEQ ID NO: 1 as is depicted in FIG. 1B (the sequence in bold), i.e. is placed directly upstream of SEQ ID NO: 1.

The fusion protein of the invention, as translated, is an antigenic recombinant fusion or chimeric protein (polypeptide) which comprises: 1) a mycobacterial HBHA protein sequence, or a functional portion thereof; and 2) an Ag85B leader peptide (or functional portion thereof) attached to or associated with the amino terminus of the HBHA protein. By "a mycobacterial HBHA protein sequence or functional portion thereof" we mean an HBHA protein with a sequence as depicted in FIG. 5B (SEQ ID NO: 4) or peptide or polypeptide fragments thereof which are antigenic, i.e. which elicit the production of antibodies which bind to native HBHA, when administered as a component of the fusion protein of the invention. Such fragments may also be sufficient to interact with and bind to heparin. For example, antigenic peptide fragments of about 50 amino acids or less in length which are comprised within about the last 30 to 50 amino acids located at the carboxyl terminus of SEQ ID NO: 4 may be employed. Peptides or polypeptides which comprise such peptide fragments may also be employed, with a polypeptide being greater than about 50 amino acids in length, but generally shorter than a full length HBHA protein. In some embodiments, such active peptide fragments may be from about 10 to about 20 amino acids in length. In other embodiments, the peptides/polypeptides may comprise or may be the 39-amino acid peptide shown below in SEQ ID NO: 5, or sequences with at least about 90% or greater (e.g. 91, 92, 93, 94, 95, 96, 97, 98, or 99%) identity to SEQ ID NO: 5. Further description of HBHA proteins and fragments thereof that may be used in the practice of the present invention is provided in issued U.S. Pat. No. 6,949,345 (Menozzi et al.), the complete contents of which is hereby incorporated by reference in entirety.

In some embodiments, the Ag85B leader sequence is attached directly to the amino terminus of the HBHA protein by virtue of the two having been translated as a single polypeptide, from tandem nucleic acid sequences within a nucleic acid molecule. In this case, the attachment is covalent and there is no intervening amino acid sequence between the leader sequence and the HBHA sequence. However, in some embodiments, relatively short (e.g. from about 1 to about 10) amino acid linker or spacer sequences may be present between the two, e.g. spacers comprising relatively small uncharged amino acids such as glycine, alanine, etc. In addition, in some embodiments, the fusion protein of the invention may have various other modifications, such as the attachment of tagging sequences e.g. to facilitate isolation or detection, e.g. affinity tags such as His tags, Isopeptag, glutathione-S-transferase (GST), chitin binding protein (CBP), maltose binding protein (MBP), etc.; solubilzation tags such as thioredoxin, MBP, GST, etc.; chromatography tags such as FLAG-tag; epitope tags such as V5-tag, c-myc-tag, HA-tag, etc.; and fluorescent tags such as various green fluorescent protein (GFP) tags and derivatives thereof, etc.

The immunogenic recombinant fusion protein sequence of the present invention is methylated, e.g. at the heparin-binding region of the HBHA. In particular, the methyl groups are carried by lysine residues present in said heparin-binding region. The sequence for said carboxy-terminal region is as follows:

KKAAPAKKAAPAKKAAPAKKAAAKKAPAKKAAAKKVTQK (SEQ ID NO: 5)

The methyl groups are carried by all or only part of the lysine residues present in the C-terminal region of HBHA. Advantageously, at least about ten lysine residues (e.g. about 10, 11, 12, 13, 14 or 15) out of the fifteen present in the C-terminal region are methylated, with the methylated lysine residues being mono- or di-methylated.

In alternative embodiments, the fusion protein of the invention may be synthesized chemically, e.g. using methodology that is well known in the art. In this embodiment, methylation is or may be carried out in vitro, e.g. as described by above-cited Pethe.

In one embodiment of the invention, the amino acid sequence of the recombinant fusion protein is: mrrlcaridi wpphtvcsgp strrhtgqrg tsmatdvsrk irawgrrlmi gtaaavvlpg lvglaggaat agafsmaens niddikapll aalgaadlal atvnelitnl reraeetrtd trsrveesra rltklqedlp eqltelrekf taeelrkaae gyleaatsry nelvergeaa lerlrsqqsf eevsaraegy vdqaveltqe algt-vasqtr avgeraaklv gielpkkaap akkaapakka apakkaaakk apak-kaaakk vtqk (SEQ ID NO: 3). In other embodiments, the amino acid sequence of the recombinant fusion protein is a sequence that is at least about 75, 80, 85, 90, 91, 92, 93, 94, 95, 96, 97, 98, or 99% identical to that of SEQ ID NO: 3, while still retaining sufficient functionality i.e. antigenicity to elicit an immune response in a subject to, whom it is administered, or still being capable of reacting in assays to detect, e.g. the presence of a latent TB infection in a patient. For example, conservative amino acid substitutions may be made in the sequence, whereby amino acids with positively charged side chains are substituted by other amino acids with positively charged side chains (e.g. lysine, histidine, arginine); or whereby amino acids with negatively charged side chains are substituted by other amino acids with negatively charged side chains (e.g. aspartic acid and glutamic acid); or whereby amino acids with hydrophobic side chains are substituted by other amino acids with hydrophobic side chains (alanine, leucine, etc.); or whereby amino acids with polar uncharged side chains are substituted by other amino acids with polar uncharged side chains (serine, threonine, etc.); and other substitutions that do not negatively impact the antigenicity of the protein. Further, certain other mutations to of deletions of or additions of single amino acids or short sequences of amino acids (e.g. about 2-5) in the sequence may be tolerated without vitiating the production and antigenicity of the fusion protein. Generally, such changes are not carried out in the heparin binding region of the protein, or at least such changes do not perturb the lysine residues which are methylated to yield the antigenic form of the protein.

The HBHA protein whose primary amino acid sequence is set forth in SEQ ID NO: 3 was identified in and derived from *M. tuberculosis* and is a native Mtb sequence. However, those of skill in the art will recognize that other HBHA proteins may also be utilized in the practice of the invention. Generally, the HBHA is identified in or derived from (i.e. is native to) a mycobacterial species or strain, for example, various strains of *M. bovis* or *M. tuberculosis*, but may come from any source so long as it functions as described herein, i.e. advantageously large quantities of the protein may be produced as described herein (e.g. at least about 10 to about 300 or more (e.g. from about 15 to about 250, or from about 20 to about 200, or from about 15 to about 150, or from about 10 to about 100 μg HBHA per mg of total protein, with the range being generally from about 30 to about 100 μs HBHA per mg of total protein). Regardless of the precise quantity, the antigenic quality of the protein is maintained, i.e. the antigenicity of the protein is comparable to that of the fusion protein represented by SEQ ID NO: 3, in terms of eliciting an immune response.

Methods of growing bacterial cultures in order to produce protein are well known in the art, as are methods of obtaining, and isolating or purifying proteins produced in this manner. The invention encompasses methods of making the fusion protein described herein by transfecting (e.g. by electroporation) a suitable mycobacterial cell, growing the transfected cell under culture conditions which are suitable for the growth of the organism and production of the protein by the organism, and then obtaining and purifying the protein. Exemplary conditions and techniques are described in the Examples section below.

In some embodiments, the nucleic acid that is introduced into the mycobacterial cell is contained within a vector such as a plasmid. However, other transfectable or transferrable vectors may be used in the practice of the invention, e.g. various viral vectors, other episomal elements, etc. In addition, in some embodiments, the nucleic acids sequences of interest may be incorporated into the genome of the *mycobacterium*.

The fusion protein that is produced and used in the practice of the present invention is, in some embodiments, substantially purified, e.g. a preparation of the protein is generally (e.g. at least 80, 90, 95, or even 99% or more) free of other proteins, as well as being free of other cellular components, e.g. nucleic acids, lipids, and other macromolecules. The rMyc of the invention may be employed as a biosource for rHBHA production and the rHBHA so-produced may be used for any purpose. In one embodiment, the purpose is to produce therapeutic immune response stimulating formulations of isolated, substantially purified fusion protein, which are discussed below.

The bacterial cells that are used in the practice of the invention may be any that fulfill the criteria of being suitable for use in a vaccine preparation. e.g. they are attenuated (i.e. decreased in virulence or disease causing capacity; rendered innocuous or incapable of causing symptoms—or causing only minor symptoms—of disease, as is understood in the art); of not displaying antibiotic resistance; and being antigenic. In some embodiments, the cells are various species or variants of *mycobacteria*, (e.g. mutant or recombinant forms) of *Mycobacterium tuberculosis, Mycotabcterium bovis, Mycobacterium smegmatis*, or other *mycobacteria*, etc. In some embodiments, the bacterial cell is *Mycobacterium bovis* BCG and/or various strains thereof, for example, mutant BCGs selected for a particular property, or recombinant BCGs that have been genetically manipulated. Exemplary recombinant BCGs are described, for example, in U.S. Pat. Nos. 7,625,572; 7,666,656; 7,829,104; and 8,043,857; all to Sun et al., the complete contents of each of which are hereby incorporated by reference. For example, the BCG may be genetically manipulated to contain and express an endosomolytic protein that is active at neutral pH (e.g. Perfringolysin O from *Clostridium perfringens*), and may also be auxotropic and not antibiotic resistant, e.g. auxotrophic for the production of leucine, pantothenate, etc., or double auxotrophs such as leucine-pantothenate auxotrophs, etc. In some embodiments, the mycobacterial cell expresses a pfo gene. Exemplary pfo genes include but are not limited to those of bacteria such as *Clostridium perfringens*. However, those of skill in the art will recognize that other functionally similar proteins exist which could also be employed in the practice of the invention, either in their wild type form, or after being genetically modified to render them suitable. Examples of such endosomalytic proteins include but are not limited to Listeriolysin (Llo, produced by *Listeria monocytogenes*), Pneumolysin (produced by *Streptococcus pneumoniae*), Streptolysin O (produced by *Streptococcus pyogenes*), Cerolysin (produced by *Bacilus cereus*), α-hemolysin (produced by *Staphylococcus aureus*), etc. In one embodiment, the cell that is employed is a pantothenate auxotroph of a BCG Danish SSI strain expressing a *Clostridium perfringens* pfo gene, referred to herein as "AERAS-413". However, those of skill in the art will recognize that other mycobactieral strains, e.g. other BCG strains such as BCG SSI without the pfo gene, Tokyo, Tice, etc., may also be employed as may those listed in, for example, U.S. Pat. No. 7,666,656, the complete contents of which is hereby incorporated by reference in entirety.

The antigenically active form of the fusion protein of the invention is methylated. Generally, methylation is carried out by and within the rMyc cell, which, in some embodiments, has a native, intrinsic capacity to produce active methytransferase enzymes. However, in some embodiments, the cell may be further modified to include nucleic acid sequences expressing additional methytransferases, or further modified to produce higher levels of native methytransferases.

The present invention also provides compositions for use in eliciting an immune response against *M. tuberculosis* and/or vaccinating an individual against tuberculosis. In one embodiment, the compositions include, as an active agent, one or more rMyc species or strains, and a pharmacologically suitable carrier. In another embodiment, the compositions include, as an active agent, one or more substantially purified fusion proteins as described herein, and a pharmacologically suitable carrier. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain various adjuvants (compounds that can induce or increase the humoral and/or cellular immune response towards an antigen or immunogen). If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of active agent in the formulations may vary. However, in general, the amount in the formulations will be from about 1-99%. Advantageously, an immunogenic composition of the invention comprises, per dose, from about 0.1 to about 50 μg of fusion protein, and generally from about 1 to 50 μg, e.g. about 15 μg of purified HBHA fusion protein. If the composition of the product comprises a live bacteria (e.g. an attenuated bacteria), the amount of bacteria per dose is generally in the range of from about $1\times10^5$ to about $1\times10^7$, and is usually about $1\times10^6$.

The compositions (preparations, formulations, etc.) of the invention may be administered by any of the many suitable means which are well known to those of skill in the art, including but not limited to by injection, intradelinally, inhalation, orally, intravaginally, intranasally, by ingestion of a food or probiotic product containing the active agent, topically, as eye drops, via sprays, etc. In some embodiments, the mode of administration is by injection or intradermally. In addition, the compositions may be administered in conjunction with other treatment modalities such as substances that boost the immune system, various chemotherapeutic agents, other antigenic agents, various adjuvants, and the like.

The invention also provides methods for eliciting an immune response in a subject in need thereof. The method involves, in one embodiment, administering a composition comprising the fusion protein of the invention, and in another embodiment, administering the rMyc of the invention. The immune response that is elicited may be one or both of innate and adaptive, and may involve both cell-mediated and humoral responses, for example, the production of antibodies, and/or a B cell and/or T cell response, etc. The response may be protective in that a recipient of the vaccine is protected against subsequent challenge with Mtb, thereby preventing the development of a TB infection, either active or latent. Further, if the compositions of the invention are administered after TB infection has occurred, the immune response may be such that a latent infection does not result, or, if a latent infection is already present, reactivation of the latent infection to active disease may be prevented, or the extent or severity of infection may be lessened.

The invention also provides diagnostic tests which utilize the fusion protein of the invention. In particular, the tests are useful for identifying individuals who have a latent tuberculosis infection. The tests typically involve exposure of the immune cells or products of immune cells of a subject identified as possibly having latent TB (e.g. due to exposure to the disease, or for some other reason) to the protein and determining whether or not the immune cells or products thereof react to or recognize the fusion protein. In one embodiment, exposure is carried out by obtaining a biological sample from the subject (e.g. saliva, sputum, blood, plasma, etc.) and exposing the sample to the fusion protein in order to detect, e.g. the presence of anti-HBHA antibodies in the sample. In another embodiment, the fusion protein is injected intradermally (e.g. in the manner of the Mantoux or other similar tests) and the reaction of the skin to the protein is observed. In both embodiments, a positive reaction to the test indicates or confirms that the subject may or is likely to have a latent tuberculosis infection.

In some embodiments the invention provides methods for producing cultures of the rMyc of the invention for use as seed lots. In particular, methods involving the batch production, purification and testing of the rMyc are encompassed. Such methods generally involve stepping up production of an initial clonal isolate, growing the isolate on a modest scale in media that is free of serum and animal origin protein, and then inoculating a culture of a desired larger volume (repeating this step as necessary until a sufficient volume is attained); and growing the rMyc culture under conditions that allow the rMyc to grow and undergo cell division. Generally, the rMyc is grown to a density ($A_{600}$) of from about 4 to about 6, e.g. about 5. Aliquots of the culture are prepared e.g. for commercial purposes, either directly from the culture, or by concentrating the rMyc (e.g. by centrifugation) and resuspending the pellet in a suitable medium. The final amount of bacteria in a seed lot culture is generally on the order of from about $4\times10^7$ to about $6\times10^7$. Those of skill in the art are familiar with techniques for the long-term maintenance of such cultures, e.g. cryopreservation, lyophilization, etc. Prior to final preparation and storage of the rMyc cultures, the rMyc identity and purity may be tested/confirmed by methods known to those of skill in the art, e.g. by sampling the culture and analyzing it for the presence of the nucleic acid which encodes the fusion protein, or by analyzing it for the presence of the fusion protein itself.

In other embodiments, the invention provides methods for producing a recombinant heparin-binding haemagglutinin (rHBHA) protein product. The methods comprise the steps of a) growing a culture of recombinant *Mycobacteria* comprising a nucleic acid fusion sequence encoding an Ag85B leader sequence attached to an amino terminus of a mycobacterial heparin-binding haemagglutinin (HBHA) protein, the fusion sequence being operably linked to a promoter, and obtaining the rHBHA protein from the culture. The *Mycobateria* may have been genetically engineered to contain and express the nucleic acid fusion sequence. Growth of the culture may be carried out in any suitable manner, e.g. in shake culture, by fermentation, etc., and the culture may be, for example, a batch or continuous culture.

The production methods typically also include a step of purifying the rHBHA protein. Purification of the protein may be carried out by any of the many suitable technologies that are known to those of skill in the art. Typically, the technology involves the use of one or more physico-chemical purification techniques. Exemplary techniques include but are not limited to: chromatography techniques such as ion exchange chromatography, affinity chromatography, size exclusion chromatography, hydrophobic interaction chromatography, etc.; as well as various cell disruption techniques such as high pressure cell disruption, the use of bead beaters, homogenization, sonication, centrifugation, etc. Combinations of these and other techniques may also be employed.

The methods may also include a step of verifying the identity of the rHBHA protein. Those of skill in the art are familiar with suitable techniques for verifying the identity and/or purity of proteins and polypeptides. Exemplary techniques include but are not limited to: electrophoresis, chromatography, mass spectrometry, amino acid sequencing, etc.

The methods may also include a step of combining purified rHBHA protein with a physiologically acceptable carrier. Suitable physiologically acceptable or compatible carriers are described elsewhere herein. In some embodiments, the formulated HBHA protein product further comprises one or more other active agents. For example, one or more antigens that are not HBHA (i.e. a non-HBHA antigen) may be included. Exemplary additional antigens include but are not limited to, for example, those which elicit an immune response against diseases such as diphtheria; pertusis; tetanus; polio, influenza, hepatitis, rotavirus, pneumonia, measles, mumps, rubella, varicella, meningitis, papillomavirus, etc. The rHBHA protein product may also include one or more adjuvants and/or one or more immunogenicity enhancers, examples of which include but are not limited to: mineral salts e.g., aluminum hydroxide ("alum"), aluminium phosphate, calcium phosphate; oil emulsions e.g., MF59, a detergent-stabilised oil-in-water emulsion; particulate adjuvants e.g., virosomes, ISCOMS (structured complex of saponins and lipids); microbial derivatives e.g., MPL™ (monophosphoryl lipid A), CpG motifs, modified toxins, etc; various plant derivatives e.g., saponins (QS-21); as well as endogenous immunostimulatory adjuvants e.g., cytokines, heat shock proteins (HSPS) and fragments thereof, etc.

The forgoing examples serve to further illustrate particular embodiments of the invention but should not be interpreted as limiting the invention in any way.

EXAMPLES

Example 1

Cloning, Over-Expression and Testing of the Heparin Binding Haemagglutinin (HBHA) in BCG The purpose of these studies was to develop a recombinant *M. bovis* BCG strain over-expressing HBHA. A recombinant BCG strain previously constructed at Aeras (AERAS-413) was used because it is a panCD auxotroph and the presence of panCD on the plasmid with the HBHA gene was used for complementation and colony selection in the absence of antibiotic resistance.

BCG Strain

Initial cloning steps were carried out in *Escherichia coli* stbl3 cells grown in LB supplemented with kanamycin (40 ug/ml). For the over expression of HBHA, a pantothenate auxotroph of a BCG Danish SSI strain expressing the pfo gene from *Clostridium perfringens* (AERAS-413) that facilitates antigen presentation through endosome escape mechanisms was utilized (1) The BCG strain was grown in Middle brook 7H9-broth and supplemented with glycerol, OADC and D-pantothenic acid (25 ug/ml). The parent and the recombinant BCG were plated on 7H10-OADC plates with and without pantothenate supplement respectively.

Design and Cloning Strategy

The Mtb sequence for HBHA gene was taken from the Tuberculist website and was synthesized (DNA 2.0) along with the Ag85B promoter and leader peptide in front of the start HBHA codon (FIGS. 1 and 2).

Figure 4:
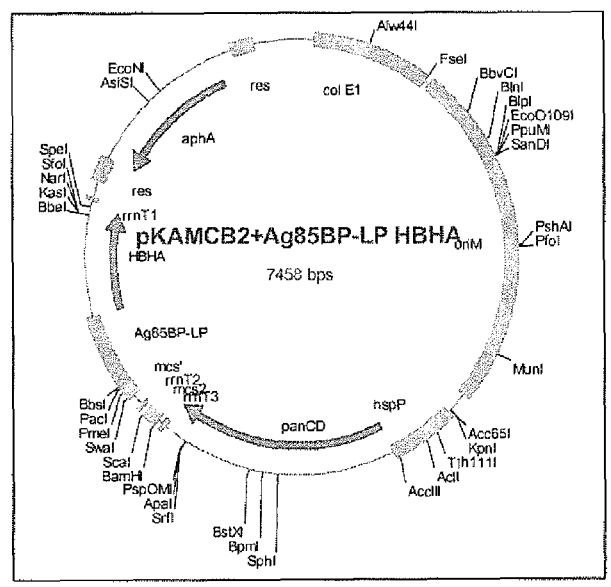
FIG. 4. Schematic showing unmarking of pKAMCB2+ HBHA clone for kanamycin resistance.

The synthesized fragment was cloned between sites PacI and SpeI in pKAMCB2 vector which is an *E. coli*-mycobacterial shuttle vector with a kanamycin resistance marker (aph) and a complementing panCD gene operated via the hsp60 promoter (FIG. 3). This plasmid was used so that it could complement the panCD auxotrophy in AERAS-413 and also maintain the stability of the plasmid in AERAS-413. Once cloned, the antibiotic marker was digested out with HpaI enzyme and the construct was self-ligated to make it "antibiotic resistant marker free" (FIG. 4). The self-ligated construct was electroporated into AERAS-413 and the recovered colonies were plated onto 7H10-plates without pantothenate supplement and without antibiotics. The colonies were screened for the presence of the antigen, the plasmid backbone and the absence of the kanamycin antibiotic resistance marker.

Amino Acid Comparison of Native and Recombinant HBHA

Native HBHA has 100% sequence identity in both BCG and Mtb. The recombinant HBHA is expressed using Ag85B promoter and Ag85B leader peptide fused to the N-terminus of the protein (FIG. 5).

Genotypic Analysis of the Colonies from AERAS-413

Figure 6C:
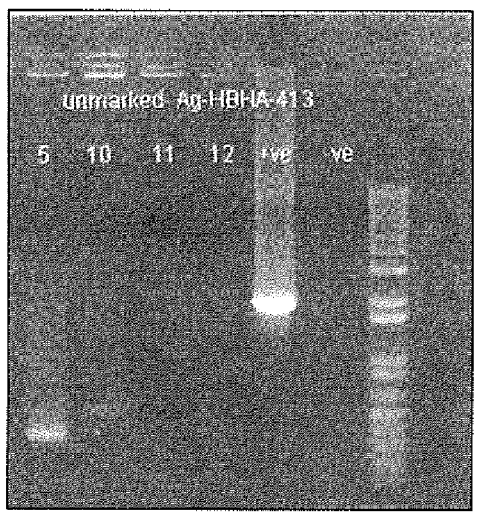

The colonies from AERAS-413 plates transformed with the pKAMCB2 derivative containing the HBHA gene were screened for the presence of the full length Ag85B-HBHA construct in the plasmid. The primers used for this PCR were Ag-HBHA for: GGTCTTCGTCGGCTTGCTTC (SEQ ID NO: 6) and Ag-HBHA.rev: GCTCTGCCAGTGTTACAACC (SEQ ID NO: 7) and the product size of 2.6 kb was expected which is seen in the colony No. 5 (FIG. 6). The same colonies were tested for the presence of the plasmid backbone spanning from the oriM to panCD complementing gene and for the absence of the antibiotic resistance marker. Primers used for the plasmid backbone were oriM7932.for GTCTACGAGGCCACACTCAG (SEQ ID NO: 8) and pan9969.rev TATCGCGCAGCTCCAGGTAG (SEQ ID NO: 9). Primers used for checking the kanamycin antibiotic marker in the plasmid were kan_intml.for GCTCGAGGCCGCGATTAAATTC (SEQ ID NO: 10) and kan_intml.rev GGATGGCAAGATCCTGGTATCG (SEQ ID NO: 11). Colony No. 5 shows the presence of the plasmid backbone and also the absence of the kanamycin gene from the backbone making it antibiotic marker less. The recombinant AERAS-413 strain over-expressing HBHA was named AERAS-445 and was used for further phenotypic analysis and scale-up manufacturing. (FIG. 6) Growth Kinetics of AERAS-445

Figure 7:
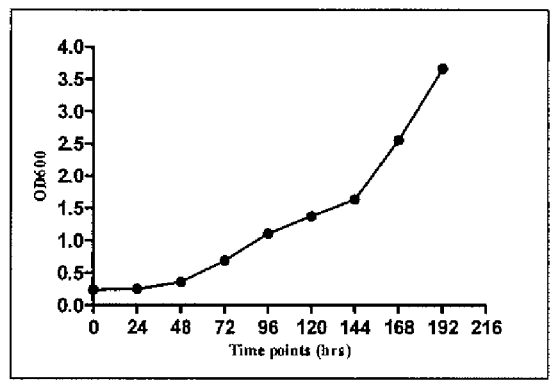
FIG. 7. Growth kinetics of AERAS 445, a pantothenate auxotroph of a BCG Danish SSI strain expression a *Clostridium perfringens* pfo gene, and further modified to encode the HBHA fusion protein of the invention.

AERAS-445 grown under conditions described above was observed to have a similar growth pattern to that of the parent strain AERAS-413 as well as AERAS-401. The seed culture was diluted to the $OD_{600}$ of 0.2 and the absorbance was measured over 9 days to observe the growth pattern. The growth pattern for AERAS-445 was very similar to that of the parent strain indicating that the over-expressed HBHA protein did not have any detrimental effect on the growth kinetics (FIG. 7)

Phenotypic Analysis of the Colonies from AERAS-413

Cultures were grown in protein-free 7H9 media to an $OD_{600}=1.0$. Cultures were spun at 3,000 rpm for ten minutes to separate the supernatant and pellets. To process the pellets for cell lysates, the pellets were resuspended in a protease inhibitor cocktail buffer and then treated by bead beating to disrupt the cells. The lysates were centrifuged at 3,000×g at 4 degrees to remove debris. Cell lysate protein concentrations were measured by BCA (bicinchoninic acid) protein assay. Normalization of samples was performed by loading equal amounts of protein, which was thirty micrograms. Samples were prepared by heating at 70 degrees for fifteen minutes with reducing agent and loading dye. Samples were then loaded onto gradient (4-12% Bis-Tris) polyacrylamide gels and run with MOPS buffer. The transfer was done using the iBlot® Dry blotting system for six minutes. Western blot analysis was done using the Snap i.d. system (Millipore). The primary antibody used was either the anti-HBHA monoclonal 4057D2 (2) (1:2000), or 1G10 (1:1000) anti-HBHA antibody followed by use of goat anti-mouse HRP secondary antibody (KPL). Detection was done by HRP chemiluminescence (Immun-Star, Biorad).

Figure 8:
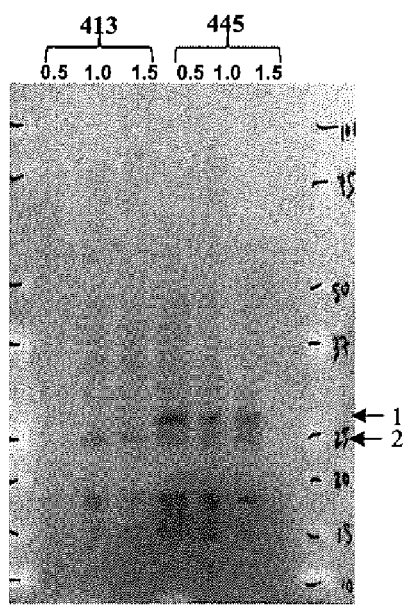
FIG. 8. Western blot showing over expression of HBHA in AERAS-445 using 4057D2 anti-HBHA monoclonal antibody. Arrows 1 and 2 indicate endogenous HBHA and recombinant HBHA proteins FIG. 9. Western blot showing over expression of HBHA in AERAS-445 using 1G10 antibody. Lanes: 1 AERAS-401; 2 AERAS-413; 3 AERAS 445. Arrows 1 and 2 indicate native HBHA and recombinant HBHA proteins FIG. 10. Western blot-HBHA expression using 1G10 antibody in different stages of manufacturing AERAS-445. Arrows 1 and 2 indicate native HBHA and recombinant HBHA proteins. Lanes: 1 AERAS 413; 2 Stage 2 manufacturing sample; 3 Accession Fermentor sample. Arrows 1 and 2 indicate endogenous HBHA and recombinant HBHA proteins FIG. 11. Yields of HBHA protein in strains determined by sandwich ELISA; A, depicted graphically, and B, depicted as a bar graph.
Figure 9:
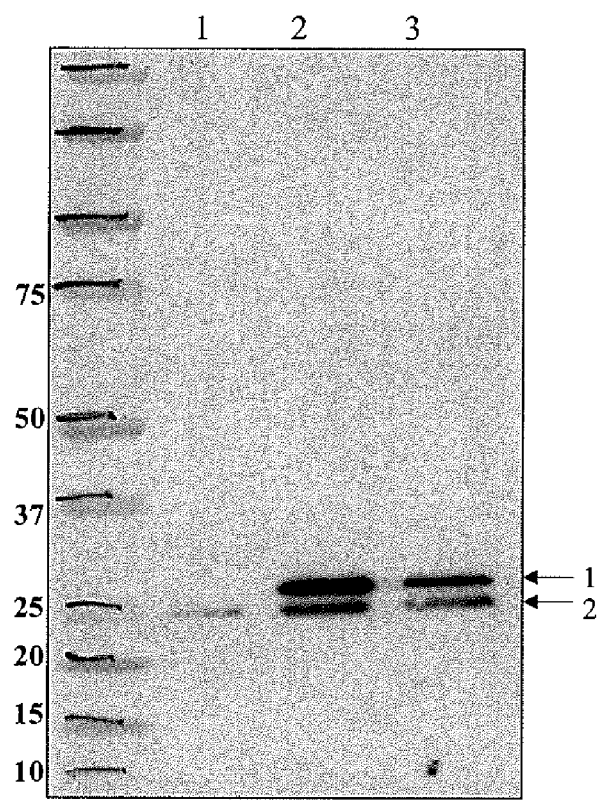

In FIG. 8, Arrow 1 indicates the recombinant HBHA in AERAS-445 and its absence in the control parent strain AERAS-413 and arrow 2 indicates the native HBHA present in both control AERAS-413 and recombinant AERAS-445. The 4057D2 monoclonal antibody, which recognizes the methylated portion of the HBHA protein, indicated that the recombinant HBHA produced in AERAS-445 is methylated. The Western blot procedure was repeated with the monoclonal antibody 1G10 developed at the Institut Pasteur de Lille, France. AERAS-401 and AERAS-413 was used as controls in this blot. Arrow 1 indicates the presence of recombinant HBHA in AERAS-445 and its absence in the control parent strains AERAS-401 and AERAS-413 and arrow 2 indicates the native HBHA is present in both the controls and recombinant strains. Unlike the 4057D2 antibody, 1G10 recognizes a specific epitope within the non-methylated region of the HBHA protein (FIG. 9).

cGMP Manufacturing of HBHA from the AERAS-445 Strain

Through a gradual reduction in animal-protein concentration, the recombinant BCG (rBCG) was adapted to grow in media free from serum and animal origin protein. The final product is a concentrated accession cell bank of 4.5±0.4 mL per vial stored at vapor phase of liquid nitrogen which can be used for the inoculation, e.g. for cGMP Master Cell Bank Production.

In order to adapt the rBCG to growing in a serum and animal origin protein free medium, the use of Oleic Albumin Dextrose Catalase (OADC) supplement in the culture medium during ACB establishment was prohibited. Table 1 summarizes the process of converting to serum animal origin protein free medium. The medium used for ACB construction was Modified Middle brook 7H9 Medium (MM7H9) without OADC or any other serum or animal derived supplement. The first stage culture was grown in a 500 mL venti-cap flask with no baffles. All cultures after the first stage were grown in baffled shaker flasks.

TABLE 1

AERAS-445 Growth Guidelines for Accession Cell Bank

| Pass/Stage | Flask Size (mL) | OADC conc. (%) | Vol. MM7H9 (mL) | Vol. OADC (mL) | Inoc. Vol. (mL) | Total Vol. (mL) | Target A600 | Centrifuge At Spec (yes/no)? |
|---|---|---|---|---|---|---|---|---|
| 1 | 500 | 0 | 95 | 0 | 5.0 | 100 | 4 ± 1.5 | No |
| 2 | 2000 | 0 | 900 | 0 | 100 | 1000 | 4 ± 1.5 | No |
| 3 | 2000 | 0 | 850 | 0 | 150 | 125 | 4 ± 1.5 | Yes |

After the culture reached its final passage, it was harvested/recovered. The culture was centrifuged at 1200×g for 30 min at 6±4° C. and re-suspended in 10% GST solution stored at room temperature at ¼ the original volume (Table 1). The culture was then dispensed in 4.0±0.5 mL aliquots into 5 mL sterile cryovials. The vials were stored in the vapor phase on liquid nitrogen.

Figure 10:
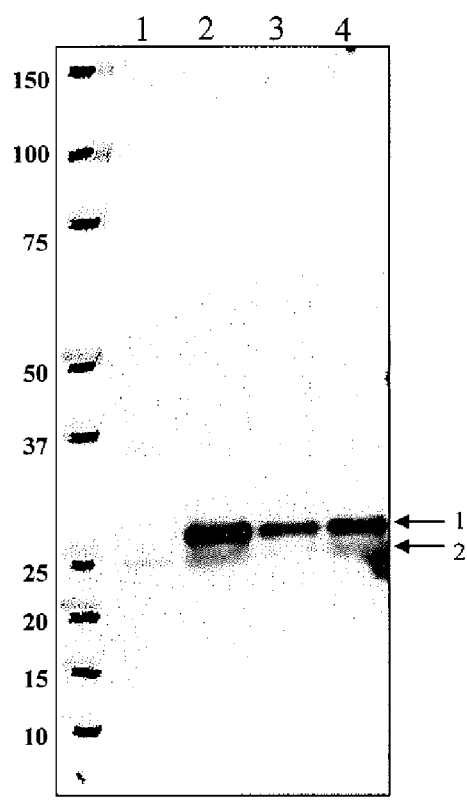
Figure 13:
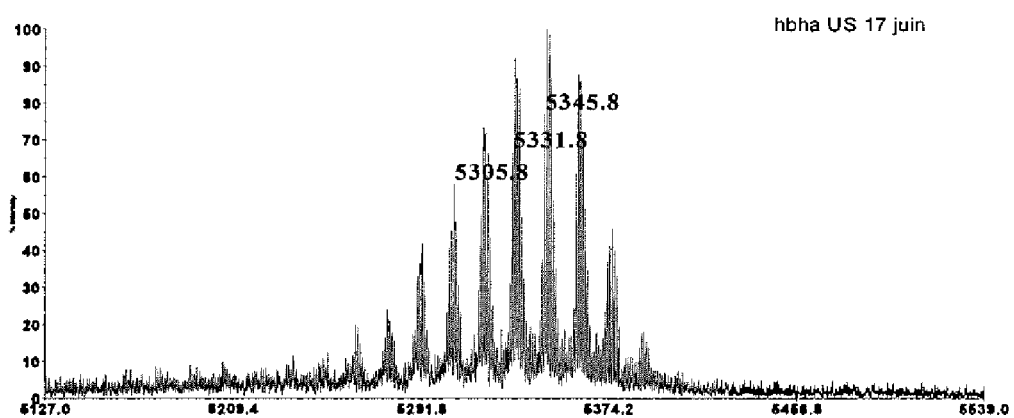
FIG. 13. Mass-spectrometry analysis of the C-terminal end of rHBHA purified from AERAS 445

Two vials of post-freeze AERAS-445 were tested for sterility. The results were negative for any growth contaminants. Vials containing 4× concentrated AERAS-445 rBCG were frozen at vapor phase liquid nitrogen. As shown in FIG. 10, a Western blot with the anti-HBHA monoclonal antibody 1G10 shows the production of the target antigen (HBHA) from cell lysates of AERAS-445 frozen cultures.

Procedure for the development of an Accession Cell Bank of AERAS 445.

1. Prepare growth media and freezing media.

| a. R&D Style Middle brook 7H9 | |
|---|---|
| 4.7 g/L | Middle brook 7H9 Powder |
| 0.24% (v/v) | Glycerol |
| 0.05% (w/v) | Tyloxapol |
| 10% (v/v) | OADC Supplement |

| b. Modified Middle brook 7H9 | |
|---|---|
| 4.7 g/L | Middle brook 7H9 Powder |
| 2.0 g/L | Sodium Glutamate |
| 2% (v/v) | Glycerol |
| 3 mg/L | Zinc Sulfate Heptahydrate |
| 0.2 g/L | Magnesium Sulfate Heptahydrate |
| 0.05% (v/v) | Tyloxapol |
| 1.0% (w/v) | Dextrose |
| 0% | OADC Supplement |

| c. 10% GST Solution | |
|---|---|
| 10% (v/v) | Glycerol |
| 0.85% (w/v) | Sodium Chloride |
| 0.05% (v/v) | Tyloxapol |

2. 5 mL of live AERAS-445 culture from Kamal Velmurugan (Vaccine Discovery) was inoculated into a 500 mL shake flask containing prewarmed 95 mL culture containing Modified Middle brook 7H9 medium without OADC.

3. For the rest of the process Modified Middle brook 7H9 medium was used.
4. The culture was incubated in a shaker/incubator (Aeras #1230) at 37° C. and 125 rpm.
5. The absorbance was measured at 600 nm when culture has a visual change in turbidity.
6. Once culture reached $A_{600}$=4.0±1.5 AU, it was inoculated into the second stage (900 mL working volume in 2 L shake flask with venti-cap) with the entire stage 1 culture (~90 mL).
7. The culture was incubated in a shaker/incubator (Aeras #1230) at 37° C. and 125 rpm.
8. The absorbance was measured at 600 nm when culture has a visual change in turbidity.
9. Once culture reached $A_{500}$=3.0±1.5 AU, it was inoculated into the Stage 3 (850 mL MM7H9 medium without OADC) with 150 mL of the Stage 2 culture. Total 3×2 L shake flasks (working volume 1 L/flask) were inoculated.
10. The culture was incubated in a shaker/incubator at 37° C. and 125 rpm.
11. The absorbance was measured at 600 nm when culture has a visual change in turbidity.
12. Once the culture (Stage 3) reached $A_{600}$=4±1.5 AU, the flask with median $A_{600}$ readout was selected and harvesting process was initiated.
13. The selected Stage 3 culture was centrifuged in a pre-autoclaved 1 l centrifuge tube for 30 minutes at 1200×g and 4° C.
14. The supernatant was discarded and the pellet was re-suspended in ¼ volume (~250 mL) of 10% GST.
15. While maintaining mixing, 5 mL cryo-vials were filled with 4.0±0.5 mL of the re-suspended cells.

The filled vials were immediately frozen in vapor phase of liquid nitrogen.

Example 2

Purification and Functional Analysis of rHBHA from AERAS-445

Estimation of the Yield of HBHA Protein in AERAS-445

The amount of HBHA produced in AERAS-445 was estimated by a sandwich ELISA method developed at the Institut Pasteur de Lille. The primary monoclonal antibody was 1G10 and the secondary monoclonal antibody was biotinylated 5F2, developed at the Institut Pasteur de Lille (EZ-link Sulfo-NHS-LC-Biotin, Pierce). In short, 100 ul per well of mAb 1 GI 0 at 5 ug/ml diluted in coating buffer was seeded on to high affinity binding ELISA plate and incubated over night at 4° C. The plate was washed twice and blocked with PBS-Tween20 (+1% BSA) for 1 hour. Recombinant and native HBHA were diluted with 1×PBS (8 dilutions) and 100 ul were added onto each well and incubated for 2 hours. After three washes with IX PBS-Tween20, 100 ul of the mAb 5F2 at a concentration of 0.2 ug/ml was added and incubated for 1 hour. The wells were washed thrice and 100 ul Streptavidin-HRP (BD biosciences) conjugate was added at concentration of 1/1000 in PBS and incubated for 30 mins at room temperature. The protein was detected with 100 μl of TMB substrate (ELISA peroxide substrate) and developed at room temperature for 5 mins to 15 mins. The reaction was stopped with 50 ul of 3M $H_3PO_4$ and the optical density was read at 450 nm. From this result AERAS-445 expressed almost 8-fold more HBHA compared to the parent strain (FIG. 11).

The yield of HBHA from the M. bovis BCG Pasteur 1173P2 was also compared with AERAS 445. The BCG strains were grown in 200 ml agitated Sauton medium in 1-liter flasks for 10 days until the optical density reading at 600 nm reached approximately 1.5. The BCG cells were then harvested by centrifugation at 8,500 rpm (Beckmann J2MC centrifuge, rotor JA10). The BCG pellet was then suspended in 20 ml PBS+0.05% Tween 80 (Tw 80: Sigma Ultra, ref. P8074) and centrifuged at 6,500 rpm (Beckman Coulter Allegra 64R, rotor F0650) for 20 min at 4° C. The pellet was the weighted before suspension in 20 ml PBS+ 0.05% Tween 80, heat inactivated and sonicated as described below. The supernatant of the sonicate was then analyzed for its protein content and for the concentration of HBHA by using the Sandwich ELISA with the monoclonal antibodies 1G10 and 5F2, as described above. An average of 3 to 4 independent measurements indicated that BCG Pasteur 1173P2 produces approximately 10 μg HBHA/mg of total protein, whereas AERAS 445 produces an average of approximately 19 μg HBHA/mg of total protein. This AERAS 445 produces roughly twice as much HBHA as BCG Pasteur 1173P2.

Purification of rHBHA from AERAS 445

Pellets of AERAS 445 were resuspended in 20 ml PBS+ OM5% Tween80 (Tw 80, Sigma Ultra, ref. P8074) and centrifuged at 6,500 rpm (Beckman Coulter Allegra 64R, rotor F0650) for 20 min. at 4° C. The pellets were weighted and resuspended in 20 ml PBS+0.05% Tween 80, heated for 30 min. at 80° C. and centrifuged for 20 min. at 12,000 rpm (Beckman Coulter Allegra 64R, rotor F0650) at 4° C.

1.5 g of heat-inactivated AERAS 445 was suspended in 15 ml PBS+0.05% Tween80 and sonicated on ice with an Analog sonifier unit model S-450A (Branson, US) for 20 min. (output 7, duty cycle 90) with a flat disruptor horn (13 mm, VWR ref. 142-3751). The sonicate was centrifuged at 13,500×g for 20 min, and the supernatant was applied onto a heparin-Sepharose CL-B column (1×5 cm) equilibrated with DPBS. The column was then washed with 100 ml DPBS, and the bound material was eluted by a 0-500 mM NaCl gradient in 100 ml DPBS. The eluted 1-ml fractions were identified by SDS-PAGE using a 12% gel followed by Coomassie Brilliant Blue R-250 staining.

The HBHA-containing fractions were pooled and applied onto a reverse-phase HPLC Nucleosil C18 column (TSK gel super ODS; Interchim) equilibrated in 0, 05% trifluoroacetic acid. Bound material was eluted with a linear 0-80% acetonitrile gradient. HBHA-containing fractions were pooled, and the solvent was eliminated by evaporation. The pH of the final fraction of 1 ml was adjusted to pH8 by using 1 M Tris-HCl (pH9). The final product was stored at −80° C. HBHA-containing fractions were analyzed by SDS-PAGE, mass spectrometry and sandwich ELISA using the 1G10 and the 5F2 monoclonal antibodies, as described above.

FIG. 12 shows a mass-spectrometry analysis of purified rHBHA from AERAS 445. For the mass-spectrometry analysis, the protein (0.1 to 10 pmol) was prepared by the dry droplet method. The protein solution (0.5 μl) was mixed with freshly dissolved a-cyano4-hydroxycinnaminic acid at 10 mg/ml in 50% $CH_3CN$ and 0.1% trifluoroacetic acid. After spotting and drying, mass spectrometry analysis was performed by using a matrix-assisted laser desorption ionization/time-of-flight (Voyager-DE-STR, Applied Biosystems). The following setting parameters were used: positive and linear modes, acceleration voltage of 25 kV, grid voltage of 92%, 750 ns of delayed extraction time, and low mass gate of 1,000 Da. The spectra were calibrated externally by using the [M+H+] monoisotopic ions of different peptides for average masses of *E. coli* thioredoxin and horse apomyoglobin (Applied Biosystems).

Mass spectrometry analysis of rHBHA methylation pattern

Purified rHBHA was digested overnight with 5% endoproteinase Glu-C(Roche), and the resulting peptides were separated by reverse-phase HPLC using a Beckman Ultra sphere ODS column (2×200 mm) and a linear 0-60% acitonitrile elution gradient prepared in 0.1% trifluoroacetic acid and directly analyzed by mass spectrometry.

For mass spectrometry, the peptide solution was mixed with freshly dissolved a-cyano4-hydroxycinnaminic acid at 10 mg/ml in 50% $CH_3CN$ and 0.1% trifluoroacetic acid. After spotting and drying, mass spectrometry analysis was performed by using a matrix-assisted laser desorption ionization/time-of-flight Voyager-DE-STR (Applied Biosystems). For peptides between 3,000 Da to 10,000 Da, the following setting parameters were used: positive and reflector modes, acceleration voltage of 25 kV, grid voltage of 65%, 250 ns of delayed extraction, and low mass gate of 1,000 Da. The spectra were calibrated externally by using the [M+H+] monoisotopic ions of different peptides for average masses of *E. coli* thioredoxin and horse apomyoglobin (Applied Biosystems).

The results of the mass spectrometry analysis of rHBHA purified from AERAS 445 are depicted in FIG. 13 and indicate that the C-terminal end of the protein shows heterogeneity, consistent with the complex methylation profile expected for HBHA.

Reaction of Different Forms of HBHA with Monoclonal Antibodies 4057D2 and 3921E4

The concentration of purified rHBHA from AERAS 445 was measured and adjusted in order to coat overnight at 4° C. 1 ng per well of ELISA plates. The plates were then washed with phosphate buffered saline (PBS)/Tween (PBST), followed by blocking for 2 hrs at room temperature with PBST containing 3% BSA. After washing again three times with PBST, the plates were incubated for 1 h30 at room temperature with serial four-fold dilutions of monoclonal antibodies 3921E4 or 4057D2 in PBST+BSA. The latter two preferentially recognize the methylated forms of HBHA (3). The plates were then washed 10 times with PBST and incubated for 1 h at room temperature with anti-mouse antibodies linked to peroxidase. After 10 additional washings with BPST, 100 μl of peroxidase substrate TMB was added to each well, and the colour reaction was stopped by the addition of 50 μl $H_3PO_4$. Finally the absorbency at 450 nm was read in each well using a standard ELISA plate reader. FIG. 14 shows that rHBHA from AERAS 445 is recognized by both the 4057D2 and the 3921E4 monoclonal antibodies, confirming that it is properly methylated.

Antigenicity of rHBHA from AERAS 445 in Latently Infected Humans

Purified rHBHA from AERAS 445 was incubated at 2 μg/ml with $10^6$ peripheral blood mononuclear cells (PBMC) isolated from three latently infected human subjects, three patients with active tuberculosis and from three negative control subjects. After 96-hours, the IFN-γ concentrations released in the supernatants were measured by ELISA, and the IFN-γ secretion from unstimulated PBMC was subtracted from the antigen-induced IFN-γ secretion. The sensitivity of the IFN-γ ELISA was 10 pg/ml. The cut-off value for optimal discrimination between non-infected controls and LTBI subjects was previously determined to be 100 pg/ml for HBHA (4). As shown in Table 2, rHBHA purified from AERAS 445 is well recognized by the PBMCs from latently infected individuals, poorly recognized by the PBMCs from tuberculosis patients and not recognized by the PBMCs from healthy controls.

TABLE 2

Human T cell antigenicity of HBHA. The PBMC from 9 human subjects (3 latently infected subjects Nos. 1, 8 and 9; three active tuberculosis patients Nos. 2, 3 and 4 and 3 negative controls Nos. 5, 6 and 7) were incubated with 2 μg/ml of HBHA from M. bovis BCG Pasteur 1173P3 (IPL) or AERAS 445 (Aeras), and the resulting IFN-g concentrations were measured in the culture supernatants and are expressed as ng/ml

| Patient Number | HBHA IPL (BCG Pasteur) | HBHA Aeras* (AERAS-445) |
|---|---|---|
| 1 | 5.21 | 13.53 |
| 2 | 0.09 | 0.02 |
| 3 | 0.02 | 0.11 |
| 4 | 0.24 | 0.27 |
| 5 | 0.07 | 0.12 |
| 6 | <0.01 | <0.01 |
| 7 | <0.01 | <0.01 |
| 8 | 1.43 | .73 |
| 9 | 1.62 | 1.28 |

REFERENCES

1. Sun R, Skeiky Y A, Izzo A, Dheenadhayalan V, Imam Z, Penn E, Stagliano K, Haddock S, Mueller S, Fulkerson J, Scanga C, Grover A, Derrick S C, Morris S, Hone D M, Horwitz M A, Kaufmann S H, Sadoff J C. Novel recombinant BCG expressing perfringolysin O and the overexpression of key immunodominant antigens; pre-clinical characterization, safety and protection against challenge with Mycobacterium tuberculosis. Vaccine. 2009 Jul. 16; 27(33):4412-23.
2. Rouse D A, Morris S L, Karpas A B, Mackall J C, Probst P G, Chaparas S D. Immunological characterization of recombinant antigens isolated from a Mycobacterium avium lambda gt11 expression library by using monoclonal antibody probes. Infect Immun. 1991 August; 59(8): 2595-600
3. Pethe et al. 2002. Mycobacterial heparin-binding hemagglutinin and laminin-binding protein share antigenic methyllysines that confer resistance to proteolysis. Proc. Natl. Acad. Sci. USA 99, 10759-10764
4. Hougardy J-M, Schepers K, Place 5, et al. Heparin-binding-hemagglutinin-induced IFN-gamma release as a diagnostic tool for latent tuberculosis. *PLoS ONE* 2007; 2: e926.
5. Temmerman S, Pethe K, Parra M, Alonso S, Rouanet C, Pickett T, Drowart A, Debrie A S, Delogu G, Menozzi F D, Sergheraert C, Brennan M J, Mascart F, Locht C. Methylation-dependent T cell immunity to *Mycobacterium tuberculosis* heparin-binding hemagglutinin. Nat Med. 2004 September; 10(9):935-41
6. Zanetti S, Bua A, Delogu G, Pusceddu C, Mura M, Saba F, Pirina P, Garzelli C, Vertuccio C, Sechi L A, Fadda G. Patients with pulmonary tuberculosis develop a strong humoral response against methylated heparin-binding hemagglutinin. Clin Diagn Lab Immunol. 2005 September; 12(9):1135-8

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A *Mycobacterium* comprising a nucleic acid fusion sequence encoding an Ag85B leader sequence attached to an amino terminus of a mycobacterial heparin-binding haemagglutinin (HBHA) protein or antigenic fragment thereof, wherein said fusion sequence is operably linked to a promoter, and wherein said nucleic acid fusion sequence comprises a nucleotide sequence at least 90% homologous to SEQ ID NO: 1.

2. The *Mycobacterium* of claim 1, wherein said *Mycobacterium* is selected from the group consisting of *Mycobacterium tuberculosis*, *Mycobacterium bovis*, and *Mycobacterium smegmatis*.

3. The *Mycobacterium* of claim 1, wherein said *Mycobacterium* is *Mycobacterium bovis* (*Bacille* Calmette-Guérin) (BCG).

4. The *Mycobacterium* of claim 3, wherein said BCG is a BCG Danish Statens Serum Institut (SSI) strain.

5. The *Mycobacterium* of claim 4, wherein said BCG SSI strain expresses a pfo gene.

6. The *Mycobacterium* of claim 5, wherein said pfo gene is a pfo gene from *Clostridium perfringens*.

7. The *Mycobacterium* of claim 1, wherein said *Mycobacterium* is an auxotroph.

8. The *Mycobacterium* of claim 7, wherein said *Mycobacterium* is a pantothenic acid auxotroph.

9. A *Mycobacterium* comprising a nucleic acid fusion sequence encoding an Ag85B leader sequence attached to an amino terminus of a mycobacterial heparin-binding haemagglutinin (HBHA) protein or antigenic fragment thereof, wherein said fusion sequence is operably linked to a promoter, and wherein a polypeptide encoded by said nucleic acid fusion sequence comprises an amino acid sequence at least 90% identical to SEQ ID NO: 3.

10. The *Mycobacterium* of claim 1, where said mycobacterial HBHA protein is *Mycobacterium tuberculosis* HBHA.

11. The *Mycobacterium* of claim 1, wherein said promoter is a mycobacterial Ag85B promoter.

12. An isolated nucleic acid molecule comprising a nucleotide sequence at least 90% homologous to SEQ ID NO: 1.

13. A fusion protein, comprising an Ag85B leader sequence attached to an amino terminus of a mycobacterial heparin-binding haemagglutinin (HBHA) protein or antigenic fragment thereof, wherein the fusion protein comprises an amino acid sequence at least 90% identical to SEQ ID NO: 3.

14. A method of producing the fusion protein of claim 13, comprising:
   transfecting a *Mycobacterium* cell with a nucleic acid sequence encoding said fusion protein; and
   growing said transfected *Mycobacterium* cell under conditions which allow said *Mycobacterium* cell to produce said fusion protein.

15. A method of producing recombinant heparin-binding haemagglutinin (rHBHA) protein, comprising the steps of:
   growing a culture of *Mycobacterium* of claim 1.

16. A seed lot of recombinant *Mycobacterium*, comprising:
   recombinant *Mycobacterium* of claim 1; and
   medium suitable for maintaining said recombinant *Mycobacterium* in a viable state during storage of said seed lot.

17. A seed lot of recombinant *Mycobacterium*, comprising:
   recombinant *Mycobacterium* of claim 9; and
   medium suitable for maintaining said recombinant *Mycobacterium* in a viable state during storage of said seed lot.

* * * * *

SEQUENCE LISTING

```
<160> NUMBER OF SEQ ID NOS: 12

<210> SEQ ID NO 1
<211> LENGTH: 825
<212> TYPE: DNA
<213> ORGANISM: Artificial Sequence
<220> FEATURE:
<223> OTHER INFORMATION: Synthetic recombinant DNA sequence encoding
      fusion protein

<400> SEQUENCE: 1
atgagacgac tttgcgcccg aatcgacatt tggcctccac acacggtatg ttctggcccg      60
agcacacgac gacatacagg acaaagggc acaagtatgg ccacagacgt gagccgaaag     120
attcgagctt ggggacgccg attgatgatc ggcacggcag cggctgtagt ccttccgggc     180
ctggtggggc ttgccggcgg agcggcaacc gcgggcgcgt tctccatggc tgaaaactcg     240
aacattgatg acatcaaggc tccgttgctt gccgcgcttg gagcggccga cctggccttg     300
gccactgtca acgagttgat cacgaacctg cgtgagcgtg cggaggagac tcgtacggac     360
acccgcagcc gggtcgagga gagccgtgct cgcctgacca agctgcagga agatctgccc     420
gagcagctca ccgagctgcg tgagaagttc accgccgagg agctgcgtaa ggccgccgag     480
```

| | | |
|---|---|---|
| ggctacctcg aggccgcgac tagccggtac aacgagctgg tcgagcgcgg tgaggccgct | 540 | |
| ctagagcggc tgcgcagcca gcagagcttc gaggaagtgt cggcgcgcgc cgaaggctac | 600 | |
| gtggaccagg cggtggagtt gacccaggag gcgttgggta cggtcgcatc gcagacccgc | 660 | |
| gcggtcggtg agcgtgccgc caagctggtc ggcatcgagc tgcctaagaa ggctgctccg | 720 | |
| gccaagaagg ccgctccggc caagaaggcc gctccggcca agaaggcggc ggccaagaag | 780 | |
| gcgcccgcga agaaggcggc ggccaagaag gtcacccaga agtag | 825 | |

<210> SEQ ID NO 2
<211> LENGTH: 1009
<212> TYPE: DNA
<213> ORGANISM: Artificial Sequence
<220> FEATURE:
<223> OTHER INFORMATION: Synthetic recombinant DNA sequence encoding
      fusion protein

<400> SEQUENCE: 2

| | | |
|---|---|---|
| gtggtcttcg tcggcttgct tcgagcgagc ctacgcggtg aacgcaagtt cggcctccct | 60 | |
| gggggagcac agccggtagc cccgggccgc gattctgaga atccgcgat agatccatac | 120 | |
| cgccataccg tttgtgagcc ccctaagcac acttgctctg tccgcggcgg taaccgatac | 180 | |
| ggaaatgaga cgactttgcg cccgaatcga catttggcct ccacacacgg tatgttctgg | 240 | |
| cccgagcaca cgacgacata caggacaaag gggcacaagt atggccacag acgtgagccg | 300 | |
| aaagattcga gcttggggac gccgattgat gatcggcacg gcagcggctg tagtccttcc | 360 | |
| gggcctggtg gggcttgccg gcggagcggc aaccgcgggc gcgttctcca tggctgaaaa | 420 | |
| ctcgaacatt gatgacatca aggctccgtt gcttgccgcg cttggagcgg ccgacctggc | 480 | |
| cttggccact gtcaacgagt tgatcacgaa cctgcgtgag cgtgcggagg agactcgtac | 540 | |
| ggacacccgc agccgggtcg aggagagccg tgctcgcctg accaagctgc aggaagatct | 600 | |
| gcccgagcag ctcaccgagc tgcgtgagaa gttcaccgcc gaggagctgc gtaaggccgc | 660 | |
| cgagggctac ctcgaggccg cgactagccg gtacaacgag ctggtcgagc gcggtgaggc | 720 | |
| cgctctagag cggctgcgca gccagcagag cttcgaggaa gtgtcggcgc gcgccgaagg | 780 | |
| ctacgtggac caggcggtgg agttgaccca ggaggcgttg gtacggtcg catcgcagac | 840 | |
| ccgcgcggtc ggtgagcgtg ccgccaagct ggtcggcatc gagctgccta agaaggctgc | 900 | |
| tccggccaag aaggccgctc cggccaagaa ggccgctccg gccaagaagg cggcggccaa | 960 | |
| gaaggcgccc gcgaagaagg cggcggccaa gaaggtcacc cagaagtag | 1009 | |

<210> SEQ ID NO 3
<211> LENGTH: 274
<212> TYPE: PRT
<213> ORGANISM: Artificial Sequence
<220> FEATURE:
<223> OTHER INFORMATION: Synthetic recombinant fusion protein

<400> SEQUENCE: 3

Met Arg Arg Leu Cys Ala Arg Ile Asp Ile Trp Pro Pro His Thr Val
1               5                   10                  15

Cys Ser Gly Pro Ser Thr Arg Arg His Thr Gly Gln Arg Gly Thr Ser
            20                  25                  30

Met Ala Thr Asp Val Ser Arg Lys Ile Arg Ala Trp Gly Arg Arg Leu
        35                  40                  45

Met Ile Gly Thr Ala Ala Ala Val Val Leu Pro Gly Leu Val Gly Leu
    50                  55                  60

```
Ala Gly Gly Ala Ala Thr Ala Gly Ala Phe Ser Met Ala Glu Asn Ser
 65                  70                  75                  80

Asn Ile Asp Asp Ile Lys Ala Pro Leu Leu Ala Leu Gly Ala Ala
             85                  90                  95

Asp Leu Ala Leu Ala Thr Val Asn Glu Leu Ile Thr Asn Leu Arg Glu
                100                 105                 110

Arg Ala Glu Glu Thr Arg Thr Asp Thr Arg Ser Arg Val Glu Glu Ser
            115                 120                 125

Arg Ala Arg Leu Thr Lys Leu Gln Glu Asp Leu Pro Glu Gln Leu Thr
        130                 135                 140

Glu Leu Arg Glu Lys Phe Thr Ala Glu Leu Arg Lys Ala Ala Glu
145                 150                 155                 160

Gly Tyr Leu Glu Ala Ala Thr Ser Arg Tyr Asn Glu Leu Val Glu Arg
                165                 170                 175

Gly Glu Ala Ala Leu Glu Arg Leu Arg Ser Gln Ser Phe Glu Glu
            180                 185                 190

Val Ser Ala Arg Ala Glu Gly Tyr Val Asp Gln Ala Val Glu Leu Thr
        195                 200                 205

Gln Glu Ala Leu Gly Thr Val Ala Ser Gln Thr Arg Ala Val Gly Glu
    210                 215                 220

Arg Ala Ala Lys Leu Val Gly Ile Glu Leu Pro Lys Lys Ala Ala Pro
225                 230                 235                 240

Ala Lys Lys Ala Ala Pro Ala Lys Lys Ala Ala Pro Ala Lys Lys Ala
                245                 250                 255

Ala Ala Lys Lys Ala Pro Ala Lys Lys Ala Ala Lys Lys Val Thr
            260                 265                 270

Gln Lys

<210> SEQ ID NO 4
<211> LENGTH: 198
<212> TYPE: PRT
<213> ORGANISM: Mycobacterium tuberculosis

<400> SEQUENCE: 4

Ala Glu Asn Ser Asn Ile Asp Asp Ile Lys Ala Pro Leu Leu Ala Ala
  1               5                  10                  15

Leu Gly Ala Ala Asp Leu Ala Leu Ala Thr Val Asn Glu Leu Ile Thr
             20                  25                  30

Asn Leu Arg Glu Arg Ala Glu Glu Thr Arg Thr Asp Thr Arg Ser Arg
         35                  40                  45

Val Glu Glu Ser Arg Ala Arg Leu Thr Lys Leu Gln Glu Asp Leu Pro
     50                  55                  60

Glu Gln Leu Thr Glu Leu Arg Glu Lys Phe Thr Ala Glu Leu Arg
 65                  70                  75                  80

Lys Ala Ala Glu Gly Tyr Leu Glu Ala Ala Thr Ser Arg Tyr Asn Glu
                 85                  90                  95

Leu Val Glu Arg Gly Glu Ala Ala Leu Glu Arg Leu Arg Ser Gln Gln
            100                 105                 110

Ser Phe Glu Glu Val Ser Ala Arg Ala Glu Gly Tyr Val Asp Gln Ala
        115                 120                 125

Val Glu Leu Thr Gln Glu Ala Leu Gly Thr Val Ala Ser Gln Thr Arg
    130                 135                 140

Ala Val Gly Glu Arg Ala Ala Lys Leu Val Gly Ile Glu Leu Pro Lys
145                 150                 155                 160
```

Lys Ala Ala Pro Ala Lys Lys Ala Pro Ala Lys Lys Ala Pro
                165                 170                 175

Ala Lys Lys Ala Ala Ala Lys Lys Ala Pro Ala Lys Lys Ala Ala Ala
        180                 185                 190

Lys Lys Val Thr Gln Lys
        195

<210> SEQ ID NO 5
<211> LENGTH: 39
<212> TYPE: PRT
<213> ORGANISM: Artificial Sequence
<220> FEATURE:
<223> OTHER INFORMATION: Synthetic peptide of carboxy terminal heparin
      binding region of HBHA

<400> SEQUENCE: 5

Lys Lys Ala Ala Pro Ala Lys Lys Ala Ala Pro Ala Lys Lys Ala Ala
1               5                   10                  15

Pro Ala Lys Lys Ala Ala Ala Lys Lys Ala Pro Ala Lys Lys Ala Ala
            20                  25                  30

Ala Lys Lys Val Thr Gln Lys
        35

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 6
ggtcttcgtc ggcttgcttc                                          20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 7
gctctgccag tgttacaacc                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 8
gtctacgagg ccacactcag                                          20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide sequence

<400> SEQUENCE: 9
tatcgcgcag ctccaggtag                                          20

```
<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 10
gctcgaggcc gcgattaaat tc                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 11
ggatggcaag atcctggtat cg                                              22

<210> SEQ ID NO 12
<211> LENGTH: 1031
<212> TYPE: DNA
<213> ORGANISM: Artificial Sequence
<220> FEATURE:
<223> OTHER INFORMATION: Synthetic recombinant DNA sequence encoding
      fusion protein

<400> SEQUENCE: 12
actgttaatt aagtggtctt cgtcggcttg cttcgagcga gcctacgcgg tgaacgcaag     60
ttcggcctcc ctgggggagc acagccggta gccccgggcc gcgattctga gaaatccgcg    120
atagatccat accgccatac cgtttgtgag ccccctaagc acacttgctc tgtccgcggc    180
ggtaaccgat acggaaatga gacgactttg cgcccgaatc gacatttggc ctccacacac    240
ggtatgttct ggcccgagca cacgacgaca tacaggacaa aggggcacaa gtatggccac    300
agacgtgagc cgaaagattc gagcttgggg acgccgattg atgatcggca cggcagcggc    360
tgtagtcctt ccgggcctgg tgggcttgc cggcggagcg gcaaccgcgg gcgcgttctc    420
catggctgaa aactcgaaca ttgatgacat caaggctccg ttgcttgccg cgcttggagc    480
ggccgacctg gccttggcca ctgtcaacga gttgatcacg aacctgcgtg agcgtgcgga    540
ggagactcgt acggacaccc gcagccgggt cgaggagagc cgtgctcgcc tgaccaagct    600
gcaggaagat ctgcccgagc agctcaccga gctgcgtgag aagttcaccg ccgaggagct    660
gcgtaaggcc gccgagggct acctcgaggc cgcgactagc cggtacaacg agctggtcga    720
gcgcggtgag gccgctctag agcggctgcg cagccagcag agcttcgagg aagtgtcggc    780
gcgcgccgaa ggctacgtgg accaggcggt ggagttgacc caggaggcgt tgggtacggt    840
cgcatcgcag acccgcgcgg tcggtgagcg tgccgccaag ctggtcggca tcgagctgcc    900
taagaaggct gctccggcca agaaggccgc tccggccaag aaggccgctc cggccaagaa    960
ggcggcggcc aagaaggcgc ccgcgaagaa ggcggcggcc aagaaggtca cccagaagta   1020
gactagttca t                                                        1031
```